US010816453B2

(12) United States Patent
Brown et al.

(10) Patent No.: US 10,816,453 B2
(45) Date of Patent: Oct. 27, 2020

(54) CO-PLANAR MICRO-IMPEDANCE CYTOMETRY DEVICE

(71) Applicant: Sharp Life Science (EU) Limited, Oxford (GB)

(72) Inventors: Christopher James Brown, Oxford (GB); Pamela Ann Dothie, Oxford (GB)

(73) Assignee: Sharp Life Science (EU) Limited, Oxford (GB)

( * ) Notice: Subject to any disclaimer, the term of this patent is extended or adjusted under 35 U.S.C. 154(b) by 292 days.

(21) Appl. No.: 15/802,596

(22) Filed: Nov. 3, 2017

(65) Prior Publication Data

US 2019/0137380 A1 May 9, 2019

(51) Int. Cl.
*G01N 15/02* (2006.01)
*G01N 15/14* (2006.01)
(Continued)

(52) U.S. Cl.
CPC ......... *G01N 15/1404* (2013.01); *G01N 15/02* (2013.01); *G01N 15/1031* (2013.01); (Continued)

(58) Field of Classification Search
CPC .............. G01N 15/1404; G01N 15/02; G01N 15/1031; G01N 15/1209; G01N 33/4836; (Continued)

(56) References Cited

U.S. PATENT DOCUMENTS 6,703,819 B2  3/2004  Gascoyne et al.
7,771,658 B2  8/2010  Larsen et al.
(Continued)

FOREIGN PATENT DOCUMENTS

WO    WO 2015-031849 A1    3/2015

OTHER PUBLICATIONS

De Ninno et al. Coplanar electrode microfluidic chip enabling accurate sheathless impedance cytometry. Lab Chip 17: 1158-1166 (Feb. 2017).*

(Continued)

*Primary Examiner* — Gailene Gabel
(74) *Attorney, Agent, or Firm* — Renner, Otto, Boisselle & Sklar, LLP

(57) ABSTRACT

An impedance cytometry device is described along with methods of accurately measuring particle size of particles contained in a fluid that is passed through the impedance cytometry device. The impedance cytometry device includes a substrate, and an electrode arrangement deposited on the substrate in a co-planar fashion. The electrode arrangement includes a drive electrode and a plurality of measurement electrodes located in a same plane as the drive electrode. The plurality of measurement electrodes includes at least two pairs of measurement sub-electrodes, each pair of measurement sub-electrodes including a first measurement sub-electrode positioned adjacent to the drive electrode, and a second measurement sub-electrode separated from the drive electrode by a respective first measurement sub-electrode. The impedance cytometry device may be incorporated into a substrate assembly of an electrowetting on dielectric (EWOD) device, such as in a substrate assembly containing electrowetting drive electrodes or a common reference electrode, or into a microfluidic blood counter device.

14 Claims, 17 Drawing Sheets

(51) Int. Cl.
  *G01N 15/10* (2006.01)
  *G01N 15/12* (2006.01)
  *G01N 33/483* (2006.01)

(52) U.S. Cl.
  CPC ..... *G01N 15/1209* (2013.01); *G01N 33/4836* (2013.01); *G01N 2015/1006* (2013.01); *G01N 2015/1409* (2013.01); *G01N 2015/1413* (2013.01)

(58) Field of Classification Search
  CPC ... G01N 2015/1006; G01N 2015/1409; G01N 2015/1413
  See application file for complete search history.

(56) References Cited

U.S. PATENT DOCUMENTS

| | | |
|---|---|---|
| 9,283,560 B2 | 3/2016 | Dothie |
| 9,440,233 B2 | 9/2016 | Dothie et al. |
| 2014/0009428 A1 | 1/2014 | Coulson et al. |
| 2016/0041081 A1 | 2/2016 | Spencer et al. |

OTHER PUBLICATIONS

De Ninno, A., et al: "Coplanar electrode microfluidic chip enabling accurate sheathless impedance cytometry" Lab Chip, 2017, 17, 1158-1166, DOI: 10.1039/c6lc01516f.

Extended European Search Report of EP 18204186.3 dated Apr. 5, 2019.

Ayliffe et al., "Electric Impedance Spectroscopy Using Microchannels with Integrated Metal Electrodes", IEEE Journal of Microelectromechanical Systems, vol. 8, No. 1, pp. 50-57 (Mar. 1999).

Gawad et al., "Micromachined Impedance Spectroscopy Flow Cytometer for Cell Analysis and Particle Sizing", The Royal Society of Chemistry, pp. 76-82 (2001).

\* cited by examiner

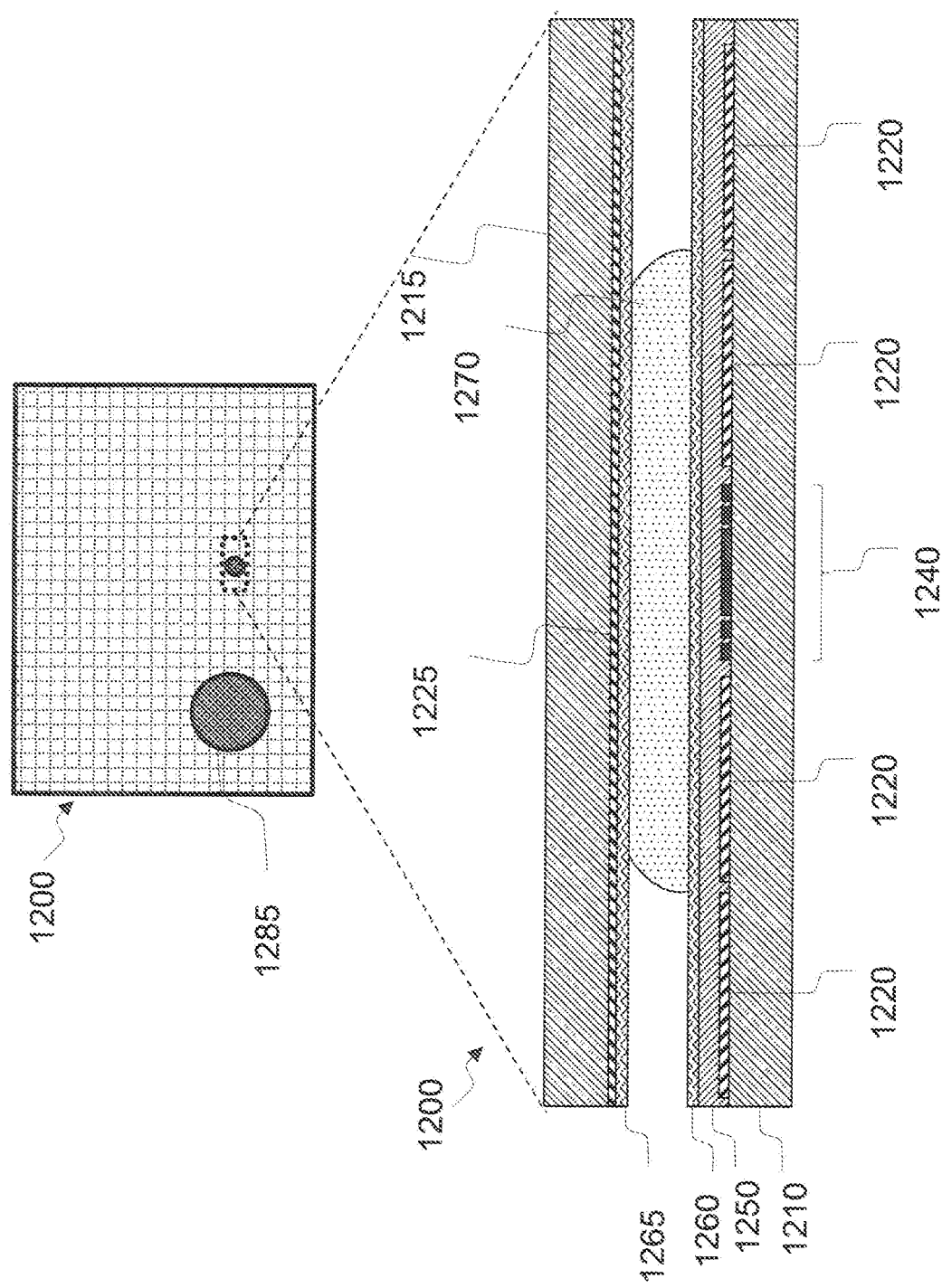

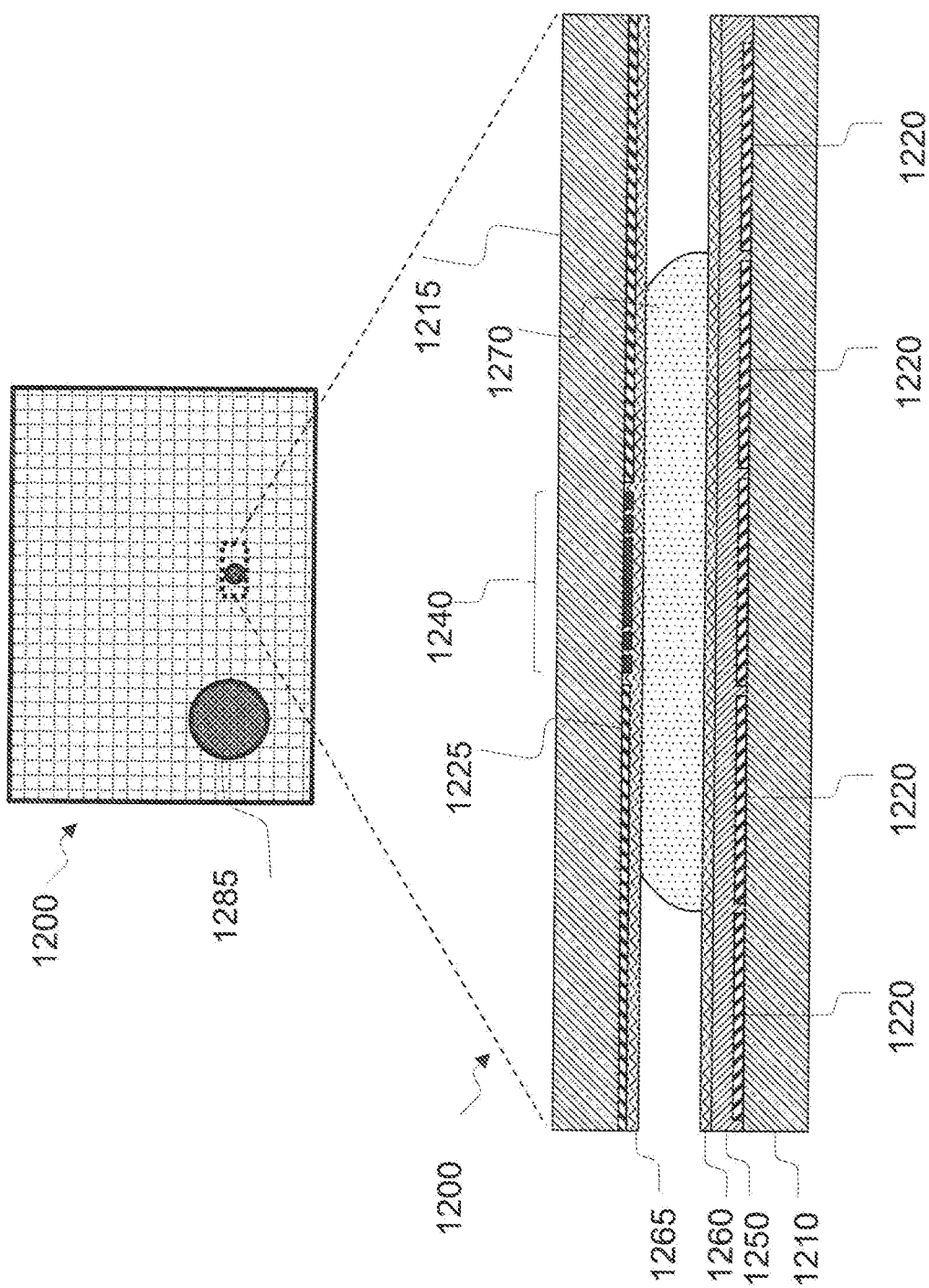

CO-PLANAR MICRO-IMPEDANCE CYTOMETRY DEVICE

TECHNICAL FIELD

The present invention is related to devices and methods for electronically detecting, counting and analyzing biological cells within microfluidic devices, including methods that can accurately discriminate among different particle types based on particle size.

BACKGROUND ART

The counting of particles flowing through a restriction, or channel, using the Coulter principle is a well-known technique. In a Coulter counter, the electrical impedance of a fluid along a channel is altered by the presence of a particle, such as a biological cell. Characteristics of the interrogating electrical signal, such as its frequency, may be modulated to provide information about the particle. Devices employing such measurement techniques may be referred to as electrical impedance spectrometry devices or impedance cytometry devices.

Ayliffe et al., Electric Impedance Spectroscopy Using Microchannels with Integrated Metal Electrodes, IEEE Journal of Microelectromechanical Systems, VOL. 8, NO. 1 (March 1999) describes a microfluidic electrical impedance spectroscopy device (impedance cytometry device). The device comprises metal electrodes and fluidic channels of micro-scale dimensions to enable the analysis of single biological cells.

Gawad et al., Micromachined Impedance Spectroscopy Flow Cytometer For Cell Analysis and Particle Sizing, The Royal Society of Chemistry (2001) describes a microfluidic electrical impedance spectroscopy device (impedance cytometry device) in which planar metal electrodes are formed on one or both sides of a micro-channel.

U.S. Pat. No. 6,703,819 (Gascoyne et al., issued Mar. 9, 2004) describes a microfluidic electrical impedance spectroscopy device (impedance cytometry device) in which sensing and driving electrodes are formed on opposite sides of a micro-channel and electrically controlled so as to increase the accuracy of the measurement.

US Patent Application 2016/0041081 (Spencer et al., published Feb. 11, 2016) describes a microfluidic electrical impedance spectroscopy device (impedance cytometry device) in which electrodes are formed on opposite sides of a micro-channel and electrically controlled so as to reduce the dependency of the measured signal on the position of the particle in the channel.

A disadvantage of conventional microfluidic impedance cytometry devices is that to increase the accuracy of the measurement it is necessary to increase the complexity of the device structure. In particular, to reduce the dependency of the measured impedance signal on the position of the particle in the channel, conventional devices employ electrodes on opposite sides of the channel. Such two-layer electrode structures result in a significant increase in the manufacturing and assembly cost of the device compared to co-planar structures in which electrodes are formed only on a single side of the channel.

SUMMARY OF INVENTION

The present invention provides a structure for a microfluidic electrical impedance spectroscopy device, also referred to as an impedance cytometry device, which is suitable for low cost manufacture and assembly, and which provides high accuracy measurements, as compared to conventional configurations. Micro-impedance cytometry is a known technique for counting and analyzing biological cells, for example human blood cells. Different types of blood cells that could be differentiated, for example, include red blood cells (RBCs), and up to the five different types of white blood cells (WBCs), including lymphocytes, neutrophils, monocytes, basophils, and eosinophils. A known issue in micro-impedance cytometry devices is that for a particle of a given size, the measured signal varies as a function of the height of the particle within the microfluidic channel. Reliably determining the cell type based on size is therefore difficult to achieve. Traditionally, sheath flows or hydrodynamic focusing techniques have been used as methods to overcome this variation in the measurement by forcing the particles to move through the center of the microfluidic channel. However, the challenges associated with focusing techniques in microfluidic channels have rendered conventional configurations deficient in accurately measuring particle sizes in a channel.

An aspect of the present invention is an enhanced micro-impedance cytometry device with a co-planar electrode structure. The described arrangement of electrodes enables an accurate measurement of the height of the particle in the microfluidic channel to be obtained. Accordingly, variations in signal magnitude due to particle height may be compensated for and an accurate measurement of the particle size may be obtained. The co-planar structure is significantly cheaper to manufacture and integrate within a sample preparation device as compared to conventional micro-impedance cytometry device structures.

In exemplary embodiments, a micro-impedance cytometry device includes a plurality of individual electrodes, that may be configured as a single drive or signal electrode and multiple sense or measurement electrodes. In one example, the electrode configuration may include a single drive or signal electrode and four sense or measurement electrodes. The sense electrodes may be arranged in two pairs on either side of the drive electrode to form four independently measurable capacitances and resultant impedances. The two sense electrodes located adjacent to the drive electrode may provide a measure of the disturbance in the electric field at the bottom of the microfluidic channel, and the remaining two sense electrodes may provide a measure of the disturbance at the top of the microfluidic channel. Impedance ratios of electrode pairs based on the measured capacitances are found to be substantially independent of cell size, and may therefore be used to compensate or correct for the measured signal magnitude to provide an accurate measurement of particle size regardless of channel height.

An impedance cytometry device is described along with methods of accurately measuring particle size of particles contained in a fluid that is passed through the impedance cytometry device. In exemplary embodiments, the impedance cytometry device includes a substrate, and an electrode arrangement deposited on the substrate in a co-planar fashion. The electrode arrangement includes a drive electrode and a plurality of measurement electrodes located in a same plane as the drive electrode. The plurality of measurement electrodes includes at least two pairs of measurement sub-electrodes, each pair of measurement sub-electrodes including a first measurement sub-electrode positioned adjacent to the drive electrode, and a second measurement sub-electrode separated from the drive electrode by a respective first measurement sub-electrode. The impedance cytometry device may be incorporated into a substrate assembly of an electrowetting on dielectric (EWOD) device, such as in a substrate assembly containing electrowetting drive electrodes, or in a substrate assembly containing a common reference electrode. The impedance cytometry device may be incorporated into a fluidic channel of a microfluidic cell counter device, such as a blood cell counter device.

Another aspect of the invention is a method of measuring particle size of particles in a fluid sample employing said impedance cytometry device. In exemplary embodiments, the measuring method includes the steps of passing the fluid sample containing particles through the impedance cytometry device; supplying a voltage stimulus to the drive electrode; measuring current signals generated on the measurement sub-electrodes to determine impedance changes generated in response to a particle passing through electric fields generated by the measurement electrodes; and determining a particle size based on the impedance changes. Features of the measuring method may include measuring differential current signals between pairs of measurement sub-electrodes. Differential current signals may be used to determine differential impedances within first regions of the microfluidic channel in which electric fields are formed between the first measurement sub-electrodes and the drive electrode, and differential impedances within second regions of the microfluidic channel in which electric fields are formed between the second measurement sub-electrodes and the drive electrode, wherein the first regions are closer to the electrode arrangement than the second regions. A ratio between peaks magnitudes of the differential impedances in the first regions and the second regions may be determined and processed to provide an accurate determination of particle size.

These and further features of the present invention will be apparent with reference to the following description and attached drawings. In the description and drawings, particular embodiments of the invention have been disclosed in detail as being indicative of some of the ways in which the principles of the invention may be employed, but it is understood that the invention is not limited correspondingly in scope. Rather, the invention includes all changes, modifications and equivalents coming within the spirit and terms of the claims appended hereto. Features that are described and/or illustrated with respect to one embodiment may be used in the same way or in a similar way in one or more other embodiments and/or in combination with or instead of the features of the other embodiments.

BRIEF DESCRIPTION OF DRAWINGS

In the annexed drawings, like references indicate like parts or features:

FIGS. 12A, 12B, and 12C are drawings depicting additional variations of operation of an impedance cytometry device integrated within an EWOD device in accordance with embodiments of the present invention; whereby in particular FIG. 12A depicts an EWOD device with an integrated impedance cytometer; FIG. 12B depicts an EWOD device for counting blood cells where the impedance cytometer is integrated into the top plate of the EWOD device; and FIG. 12C depicts an EWOD device for counting blood cells where the impedance cytometer is integrated into the bottom plate of the EWOD device.

DESCRIPTION OF EMBODIMENTS

Figure 1:
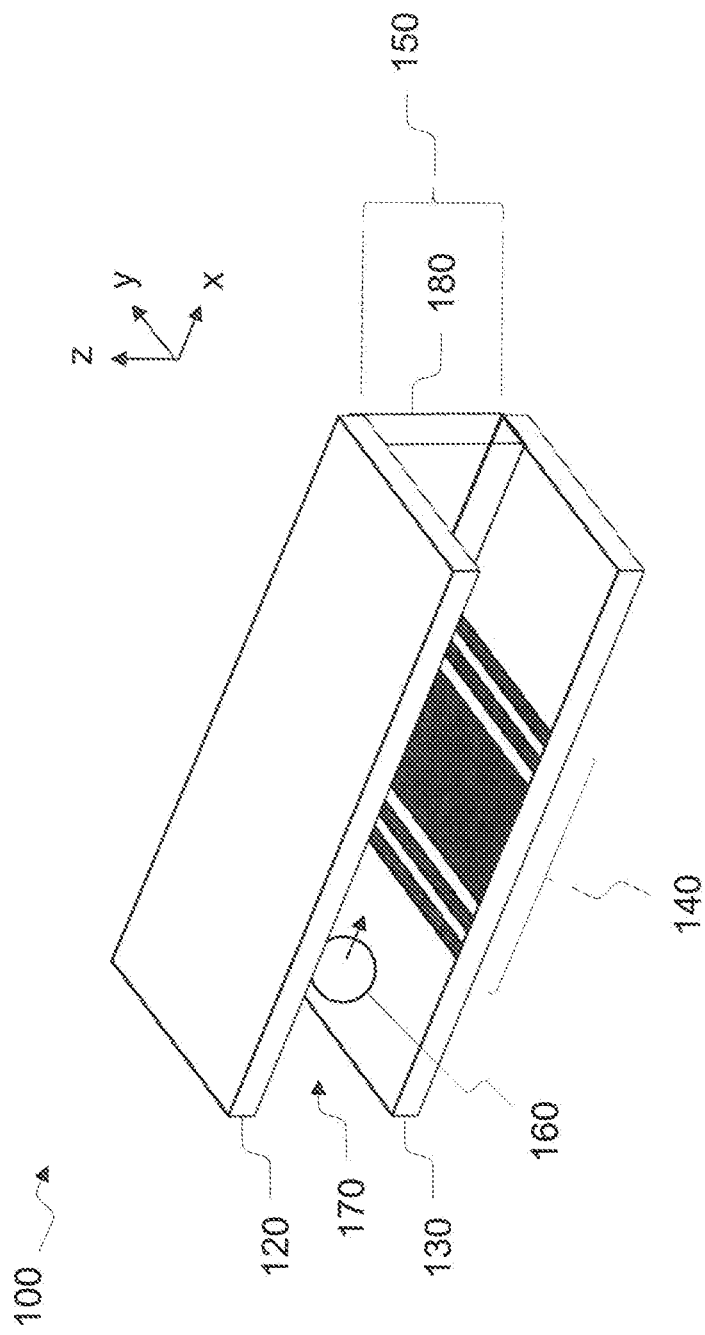
FIG. 1 is a drawing depicting an arrangement of electrodes and microfluidic channel in accordance with embodiments of the present invention.

Embodiments of the present invention will now be described with reference to the drawings, wherein like reference numerals are used to refer to like elements throughout. It will be understood that the figures are not necessarily to scale.

In an exemplary embodiment of a first aspect of the present invention, a microfluidic impedance cytometry device is provided wherein electrodes for performing the measurement of particles in the microfluidic channel are positioned on a single planar surface and arranged so as to provide a measurement of the particle that is independent of the position of the particle in the microfluidic channel.

FIG. 1 is a drawing depicting an arrangement of electrodes and microfluidic channel in accordance with embodiments of the present invention. A microfluidic device 100 includes a first substrate 130 and a second substrate 120 which may be arranged to oppose the first substrate 130 and to form a gap or microfluidic channel 150 between the substrates. The microfluidic channel 150 may be defined by a spacer 180. The first substrate 130 and the second substrate 120 may be made of a glass or plastic material. The first substrate 130 and second substrate 120 may be of the same or of different materials. The spacer 180 may be a plastic, glue or photoresist material. Alternatively, the spacer 180 may be part of the first substrate 130 or part of the second substrate 120, for example a feature of the second substrate formed during a manufacturing process such as machining or injection molding.

The spacer 180 may be patterned so as to define the microfluidic channel along which a fluid 170 containing particles 160 to be measured may flow. In such case, a width of the channel may be chosen to be larger than, but of a similar magnitude to, the diameter of the particles 160 to be measured. In such case the channel width may, for example, typically be in the range of 1-100 μm. As is well-known in the art, a height (z) of the gap may be chosen to be larger than, but of a similar magnitude to the diameter of, the particles 160 to be measured. For example, the diameter of particles 160 to be measured may typically be in the range of 0.5-50 μm and the height of the gap may be in the range of 1-100 μm. The microfluidic channel 150, therefore, may be configured along with control of the particle concentration in the fluid to ensure that generally a single particle is present at any particular (x, y) position in the channel gap and that the channel gap does not become blocked by particles.

Electrodes 140 are formed on the first substrate 130 in the region of the gap 150. The electrodes may be in direct and therefore resistive electrical contact with the fluid present in the microfluidic channel. In such case the electrodes may be formed from a conductive material that is known to be inert, such as, for example, platinum, gold or the like. Alternatively, an insulator film may be formed over the electrodes such that there is no direct electrical contact between electrodes and the fluid. The electrodes are instead in indirect and therefore capacitive electrical contact with the fluid and deleterious effects, such as leakage resistance between electrodes, may be minimized. In such case the electrodes may be formed from any suitable conductive material and the insulator may be of a well-known type such as silicon dioxide, silicon nitride or aluminum oxide.

Generally, with reference to subsequent figures, exemplary embodiments of an impedance cytometry device are described along with methods of accurately measuring particle size of particles contained in a fluid that is passed through the impedance cytometry device. In exemplary embodiments, the impedance cytometry device includes a substrate, and an electrode arrangement deposited on the substrate in a co-planar fashion. The electrode arrangement includes a drive electrode and a plurality of measurement electrodes located in a same plane as the drive electrode. The plurality of measurement electrodes includes at least two pairs of measurement sub-electrodes, each pair of measurement sub-electrodes including a first measurement sub-electrode positioned adjacent to the drive electrode, and a second measurement sub-electrode separated from the drive electrode by a respective first measurement electrode. The impedance cytometry device may be incorporated into a substrate assembly of an electrowetting on dielectric (EWOD) device, such as in a substrate assembly containing electrowetting drive electrodes, or in a substrate assembly containing a common reference electrode.

Figure 2:
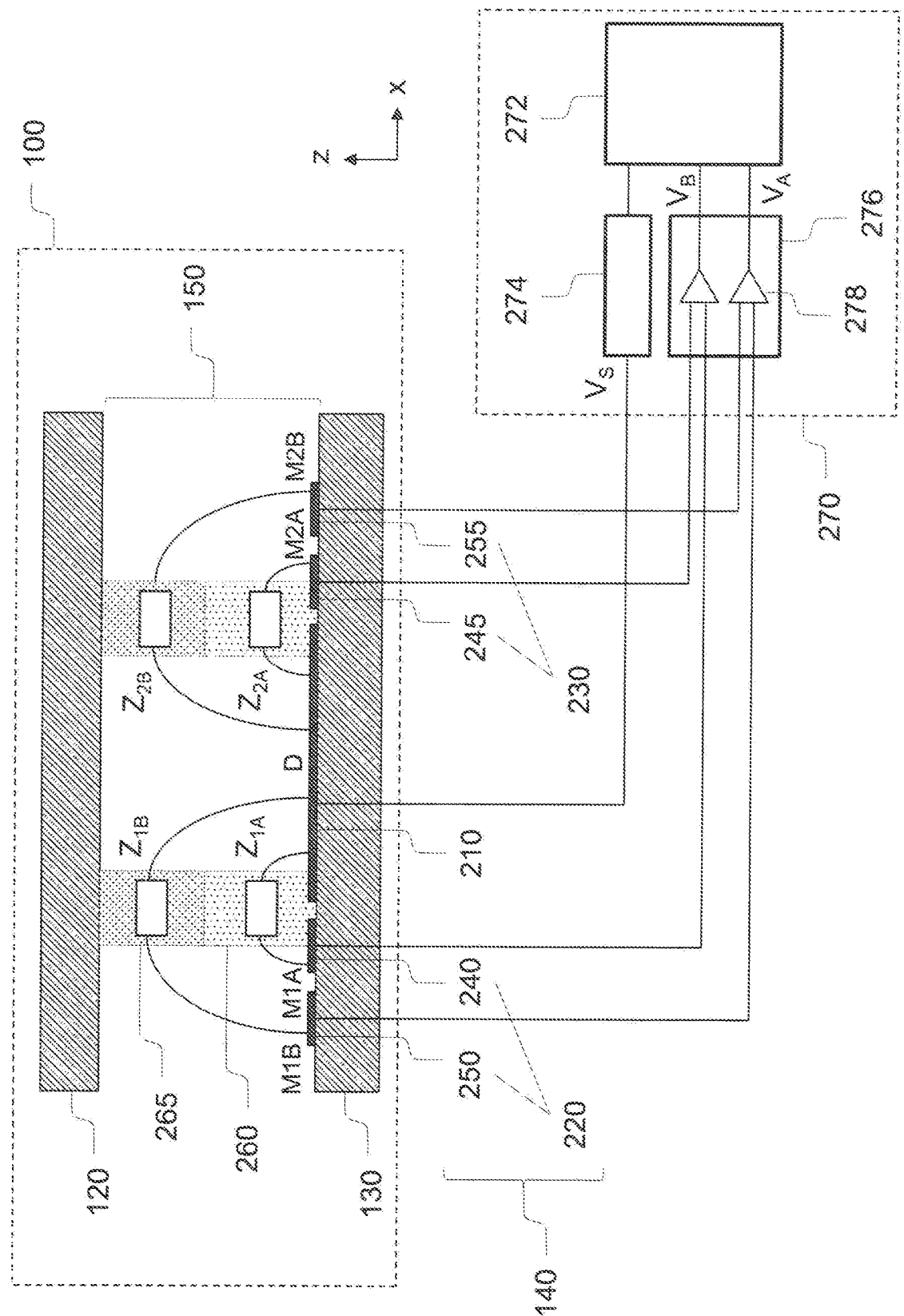
FIG. 2 is a drawing depicting a cross-section diagram of an exemplary microfluidic device in accordance with embodiments of the present invention.

FIG. 2 is a drawing depicting a cross-section diagram of the microfluidic device 100 illustrating the electrical arrangement of the electrodes 140 and the electric field in the gap between the first and second substrates 120 and 130 in the region of the electrodes. The electrode arrangement 140 may be deposited on one of the substrates, e.g., substrate 130, in a coplanar fashion. The electrodes 140 may include a drive electrode 210 and a plurality of measurement electrodes located in a same plane as the drive electrode. The plurality of measurement electrodes may include at least two pairs of measurement sub-electrodes, such as for example a first set of measurement electrodes 220 and a second set of measurement electrodes 230 arranged on opposite sides of the drive electrode 210. In the example of FIG. 2, each of the two pairs of measurement electrodes 220, 230 may further include a first measurement sub-electrode 240, 245 and a second measurement sub-electrode 250, 255. Within each set of measurement electrodes 220, 230, the first measurement sub-electrodes 240, 245 may be positioned adjacent to the drive electrode 210, and the second measurement sub-electrodes 250, 255 may be separated from the drive electrode 210 by the respective first measurement sub-electrode 240, 245. In this example arrangement, each of the first measurement sub-electrodes 240, 245 forms a first impedance $Z_{1A}$, $Z_{2A}$ with the drive electrode 210. Each of the second measurement sub-electrodes 250, 255 forms a second impedance $Z_{1B}$, $Z_{2B}$ with the drive electrode 210.

First regions 260 of the gap or microfluidic channel 150 (denoted by a first shading pattern in the figure) may be defined as an area in a lower portion of the gap and between the drive electrode (D) 210 and the sets of measurement electrodes 220, 230, with some overlap of the sets of measurement electrodes within the channel. Similarly, second regions 265 of the gap or microfluidic channel 150 (denoted by a second shading pattern in the figure) may be defined as an area in an upper portion of the gap 150 and between the drive electrode 210 and the set of measurement electrodes 220, 230, also with some overlap of the sets of measurement electrodes within the channel, With the orientation of FIG. 2, therefore, the directional indication of the first region 260 being in the lower portion of the gap means the first region 260 is adjacent to the first substrate 130. Similarly, with the orientation of FIG. 2, the directional indication of the second region 265 being in the upper portion of the gap means the second region 265 is adjacent to the second substrate 120.

The first measurement sub-electrode (M1A, M2A) 240, 245 in each set of measurement electrodes is arranged such that the electric field lines associated with the electrical field coupling a respective first measurement sub-electrode and the driving electrode 210 are substantially present in only the first regions 260. Accordingly, the associated first impedances, $Z_{1A}$ and $Z_{2A}$, may be used as a measure of disturbances in the electric field associated with a particle passing through the first regions 260. The second measurement sub-electrode (M1B, M2B) 250, 255 in each set of measurement electrodes is arranged such that the electric field lines associated with the electrical field coupling a respective second measurement sub-electrode and the driving electrode 210 are substantially present in only the second regions 265. Accordingly, the associated second impedances, $Z_{1B}$ and $Z_{2B}$, may be used as a measure of disturbances in the electric field associated with a particle passing through the second regions 265.

The effect described above is achieved when the width and separations of the measurement sub-electrodes in the x-dimension along the microfluidic channel 150 are chosen to be of a similar magnitude to both the gap 150 between the first substrate 130 and second substrate 120 and the diameter of the particles to be measured. For example, the width and separations of the measurement sub-electrodes may typically be in the range of 1-50 μm. For the impedances associated with the first and second sets of measurement electrodes on either side of the drive electrode to be independently measured, the size of the drive electrode in the x-dimension may be chosen to be of a magnitude which is a multiple of both the gap 150 and the diameter of the particles to be measured.

In operation, a fluid containing particles is forced to flow along the microfluidic channel 150 such that the particles pass by the electrodes 140. The concentration of particles in the fluid may be chosen such that only one particle passes by the electrodes at any one time. The resulting changes in the impedances, $Z_{1A}$, $Z_{1B}$, $Z_{2A}$ and $Z_{2B}$, associated with the first and second sets of measurement electrodes may be measured by an impedance measurement unit 270 that is configured to measure impedance differences between measurement sub-electrodes of the plurality of measurement electrodes.

The impedance measurement unit 270 may include a control unit 272 coupled to both a voltage stimulus unit 274 and a sensing unit 276. As is well-known in the art, the voltage stimulus unit 274 may be arranged to apply a driving voltage signal (Vs), for example a sinusoidal voltage stimulus of fixed amplitude and frequency, to the drive electrode 210. The sensing unit 276 may be arranged to measure the current signal generated on the measurement sub-electrodes in response to the voltage stimulus. The current signal of each measurement sub-electrode may be measured independently. Alternatively, a difference signal between pairs of measurement sub-electrodes may be measured using separate differential sensing circuits 278 within the sensing unit 276 that are configured to measure differential current signals between the different measurement electrodes. For example, as shown in FIG. 2, the differential current signals between the first measurement sub-electrodes 240, 245 in the first and second sets of measurement electrodes 220, 230, and between the second measurement sub-electrodes 250, 255 in the first and second sets of measurement electrodes 220, 230 may be measured. Alternatively, the differential current signals between the first and second sub-electrodes within each measurement set may be measured. The control unit 272 may be arranged to receive output signals form the sensing unit, and to convert and process the output signals (for example $V_A$ and $V_B$) of the sensing unit 276 to calculate impedance differences and provide a measurement of particles passing the electrodes that is independent of the particle position within the gap.

In a conventional microfluidic impedance cytometry device with a co-planar electrode arrangement, the magnitude of the measured impedance signal is a function of both the particle diameter and the particle position in the gap in the z-direction that extends between the substrates. Accordingly, it is substantially difficult to accurately discriminate between particles of different diameters. Since fluid samples to be analyzed typically contain particles of many different sizes and types, conventional devices therefore have a significant disadvantage in that conventional devices cannot be used to reliably distinguish and count cells (e.g. blood cells, bacteria etc.) of a particular type. As further described below, an advantage of the present invention is that the device configured as disclosed may be used to reliably distinguish between and count particles of different sizes, or size ranges, corresponding to different types of particles to enable discriminating among different types of particles. For example, the present invention may discriminate between platelets, red blood cells and white blood cells (lymphocytes, neutrophils, monocytes, basophils and eosinophils) in a sample of human or animal blood.

An aspect of the invention is a method of measuring particle size of particles in a fluid sample employing said impedance cytometry device. In exemplary embodiments, the measuring method includes the steps of passing the fluid sample containing particles through the impedance cytometry device; supplying a voltage stimulus to the drive electrode; measuring current signals generated on the measurement electrodes to determine impedance changes generated in response to a particle passing through electric fields generated by the measurement electrodes; and determining a particle size based on the impedance changes. Features of the measuring method may include measuring differential current signals between pairs of measurement sub-electrodes. Differential current signals may be used to determine differential impedances within first regions of the microfluidic channel in which electric fields are formed between the first measurement sub-electrodes and the drive electrode, and differential impedances within second regions of the microfluidic channel in which electric fields are formed between the second measurement sub-electrodes and the drive electrode, wherein the first regions are closer to the electrode arrangement than the second regions. A ratio between peaks magnitudes of the differential impedances in the first regions and the second regions may be determined and processed to provide an accurate determination of particle size.

Figure 3A:
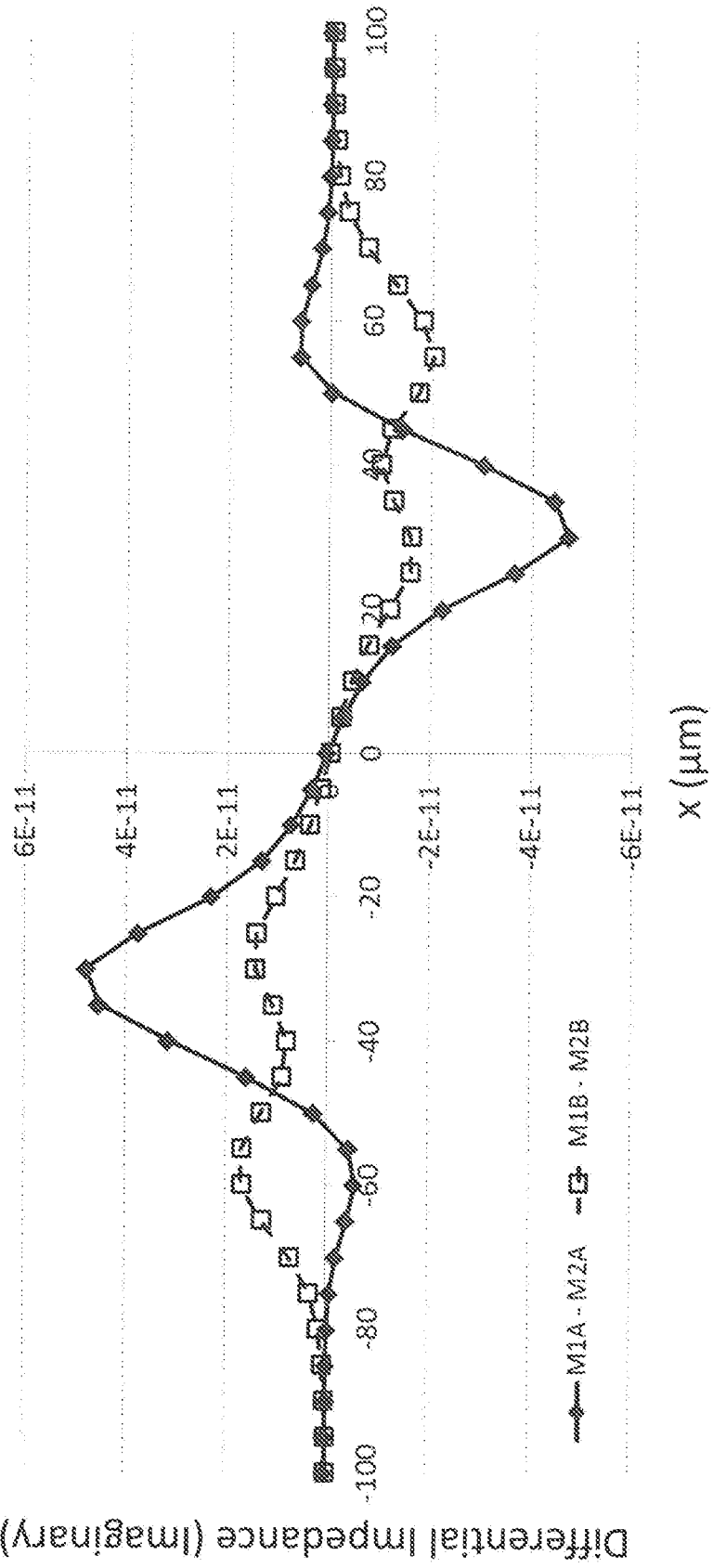
FIG. 3A is a graph depicting an example of measured impedance signals generated in response to a particle passing through first regions of the microfluidic device of FIG. 2.
Figure 3B:
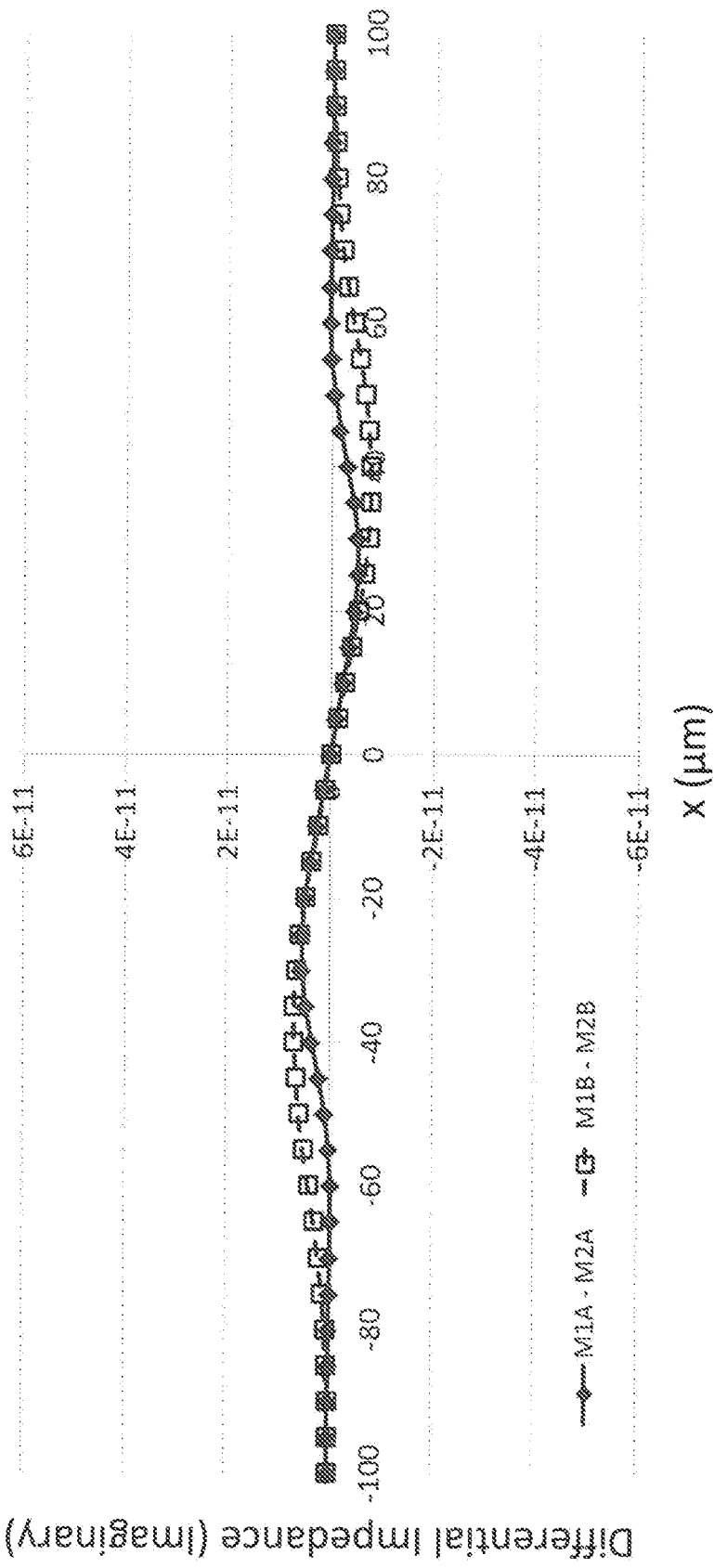
FIG. 3B is a graph depicting an example of measured impedance signals generated in response to a particle passing through second regions of the microfluidic device of FIG. 2.

FIG. 3A shows an example of measured impedance signals generated in response to a particle passing through the first regions 260 of the gap 150 of the microfluidic device 100 illustrated in FIG. 2. As denoted in FIG. 2, the x-axis direction is the direction along the microfluidic channel or gap 150, and the x-axis zero position is designated to be the position coincident with a center line of the drive electrode 210. The solid line represents the imaginary component of the differential impedance measured between the first measurement sub-electrodes 240, 245 in the first and second sets of measurement electrodes 220, 230 (M1A-M2A). Said differential impedance may be, for example, derived from the output of the differential sensing unit 276 as a function of the voltage output signals $V_A$ and $V_B$. The dotted line represents the imaginary component of the differential impedance measured between the second measurement sub-electrodes 250, 255 in the first and second sets of measurement electrodes 220, 230 (M1B-M2B). FIG. 3B shows an example of measured impedance signals generated in response to a particle passing through the second regions 265 of the gap 150. The solid line and dotted lines represent similar measurements as described above for FIG. 3A.

Figure 4:
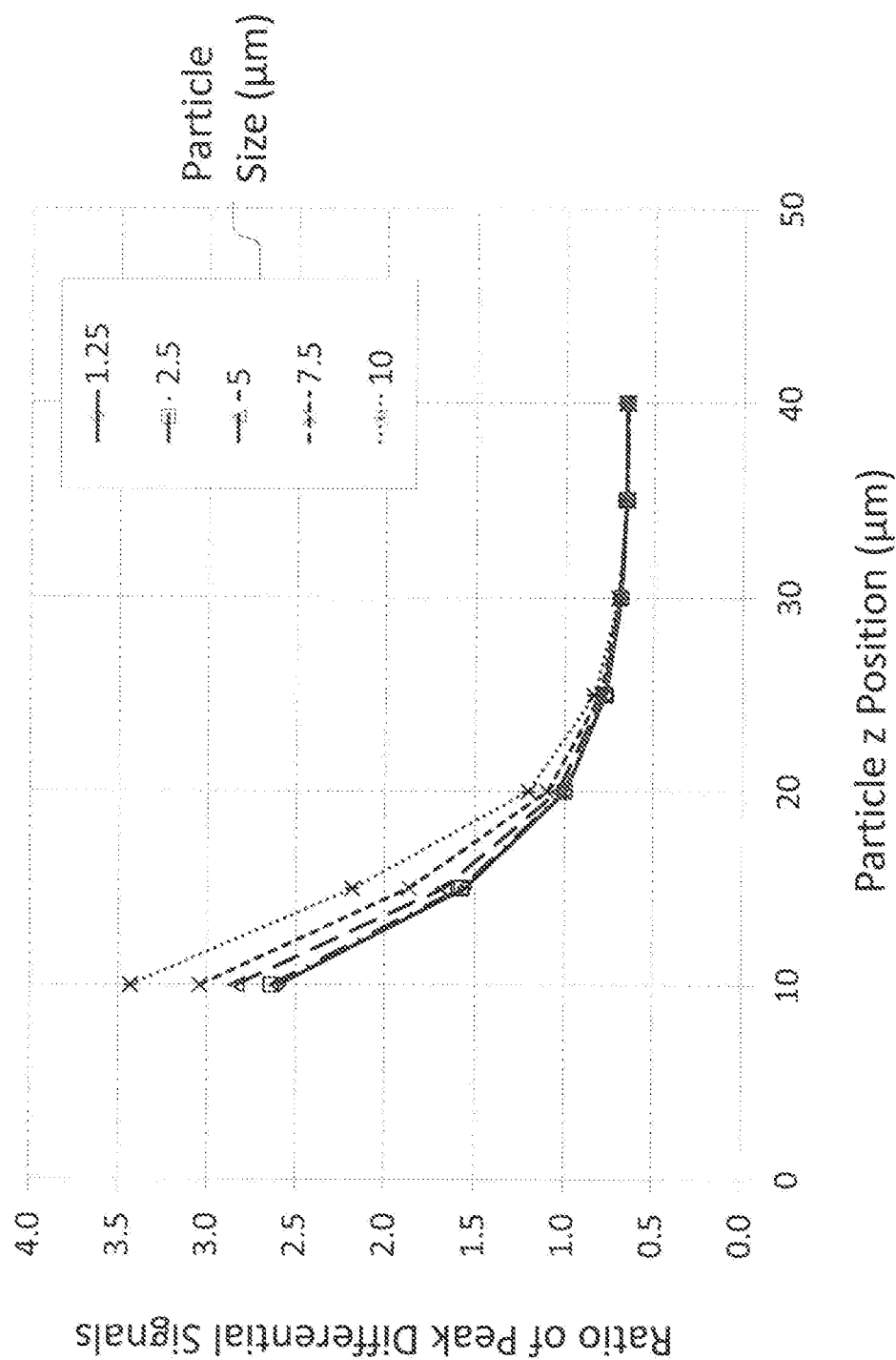
FIG. 4 is a graph depicting a ratio of the peak magnitudes of two measured differential impedances being approximately constant across a wide range of particle diameters.

As shown by comparison of the relative peak magnitudes of the solid and dotted lines in FIG. 3A and FIG. 3B, particles passing by the electrodes in the lower portion of the gap cause a relatively larger maximum change in the first measured impedances, $Z_{1A}$ and $Z_{2A}$, than the second measured impedances, $Z_{1B}$ and $Z_{2B}$. Conversely, particles passing by the electrodes in the upper portion of the gap may cause a relatively larger maximum change in the second impedances than the first impedances. The inventors have found that such measurements may be employed for enhanced particle discrimination. As shown in FIG. 4, it is observed that a ratio of the peak magnitudes of the two measured differential impedances is approximately constant across a wide range of particle diameters. In FIG. 4, said ratio is plotted as a function of position within the microfluidic channel or gap. As denoted in FIG. 2, the z-axis direction is the direction perpendicular to the electrode plane through the microfluidic channel or gap 150, and the z-axis zero position is designated to be the position coincident with the surface of the substrate 130. As seen in FIG. 4, the ratio curves among the representative particle sizes are largely comparable, with the differences being insignificant for determining particle size. The graph of FIG. 4 shows that the differential peak magnitude ratio is essentially the same regardless of particle size at a given position within the gap 150 in the z-direction.

Accordingly, the measured impedance signals may be processed to produce an accurate count of particles of a particular diameter, or particular range of diameters, passing by the electrodes that is independent of particle position in the gap in the z-direction. A processed impedance value can be calculated as a function of output voltages based on the measured differential impedances, including using the referenced ratio of the peak magnitudes of the two measured differential impedances. The processed impedance value can then be associated with particle size in a manner that is accurate and is independent of a particle's position within the microfluidic channel. For the example arrangement shown in FIG. 2, the output signals $V_A$, $V_B$ or the sensor unit 276 may be processed to achieve this effect by application of an equation of the following form:

$$Z = (\max(V_A(t) + V_B(t))) \cdot \left(\frac{\max(V_A(t))}{\max(V_B(t))}\right)^{-n}$$

where:
Z is the processed output value
$V_A(t)$ is the first output voltage signal from the sensor unit
$V_B(t)$ is the second output voltage signal from the sensor unit
n is a scaling factor which may be empirically derived.

Figure 5A:
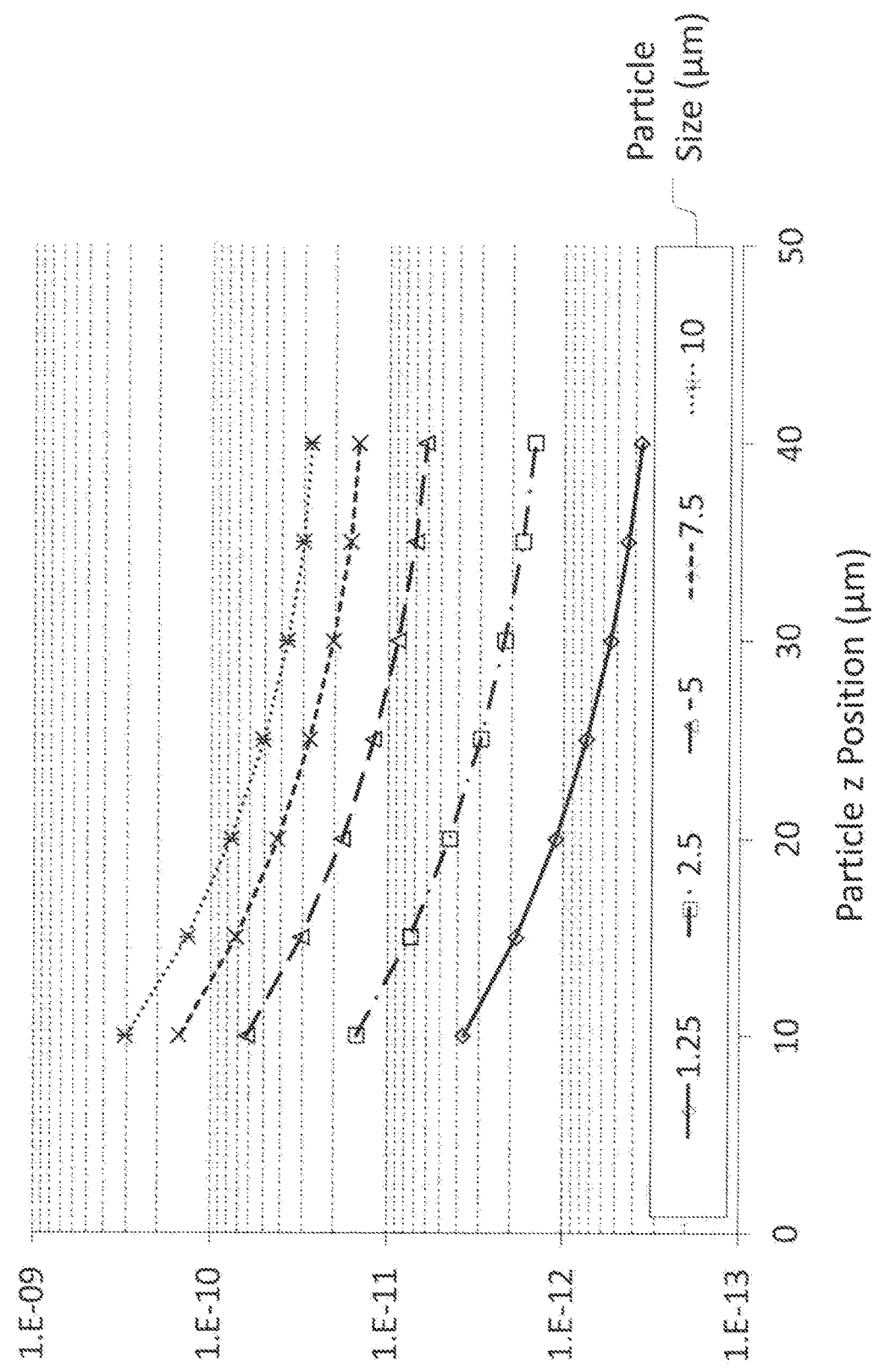
FIG. 5A is a graph depicting typical raw uncorrected impedance measurement results as a function of particle size and position in a microfluidic channel.
Figure 5B:
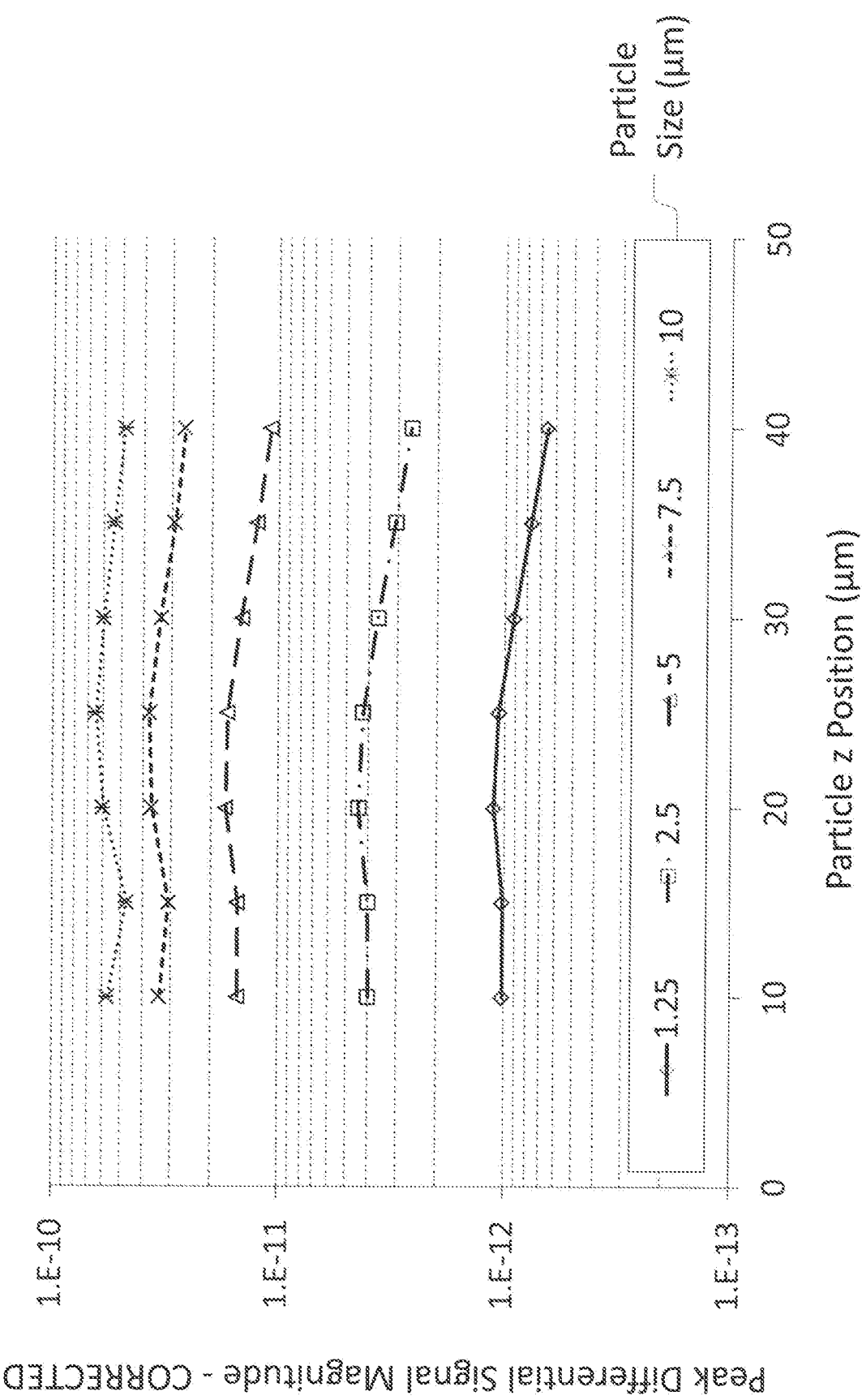
FIG. 5B is a graph depicting corrected impedance measurement results arising from processing the uncorrected results in accordance with embodiments of the present invention.

An example of the effect of applying such a processing method to the measured impedance signals is illustrated in FIG. 5A and FIG. 5B. FIG. 5A is a graph that depicts typical raw uncorrected impedance measurement results as a function of particle size and z-position in the microfluidic channel. The y-axis data represents the peak of the sum of the differential measurements i.e. $\max(V_A(t)+V_B(t))$. The scaling factor is determined by taking the data used to plot FIG. 5A and setting 'n' as a variable parameter. One then changes 'n' until the plot changes from a curve (FIG. 5A) to the approximately parallel lines seen in FIG. 5B. Ideally, there will be distinct "bands" where Z (the processed output value) for a given particle diameter, e.g. 10 um, does not overlap with the Z (processed output value) for a second e.g. 7.5 um diameter particle. The scaling factor 'n' can be changed manually or a program can be written to automatically determine the 'n' value that provides the best distinction between the processed output values for different particle sizes, e.g., aiming to minimize the chance of there being overlapping max/min values for the two or more different particle sizes that have to be differentiated with unique output values.

It is noted that this uncorrected plot is equivalent to that generated from a conventional co-planar electrode arrangement. As shown by the plot, particles of different sizes and at different positions in the gap may generate similar uncorrected measurement results and therefore be indistinguishable from each other. Accordingly, conventional configurations are unable to distinguish among different particles based on particle size.

On the other hand, FIG. 5B is a graph that depicts corrected impedance measurement results arising from processing the uncorrected results using the above equation. As can be seen, a particle of a particular size results in a unique output value, or range of output values, for all positions in the gap in the z-direction, which permits distinguishing among different particles based on particle size.

Subsequent FIGS. 6A-10 show alternative configurations or optional features of an impedance cytometry device and related EWOD devices based on comparable principles as above. It should be noted that for simplicity, the impedance measurement unit 270 and its associated components are omitted in the subsequent figures. It will be appreciated that comparable measurement and control structures may be employed in combination with any of the embodiments of FIGS. 6A-10.

Figure 6A:
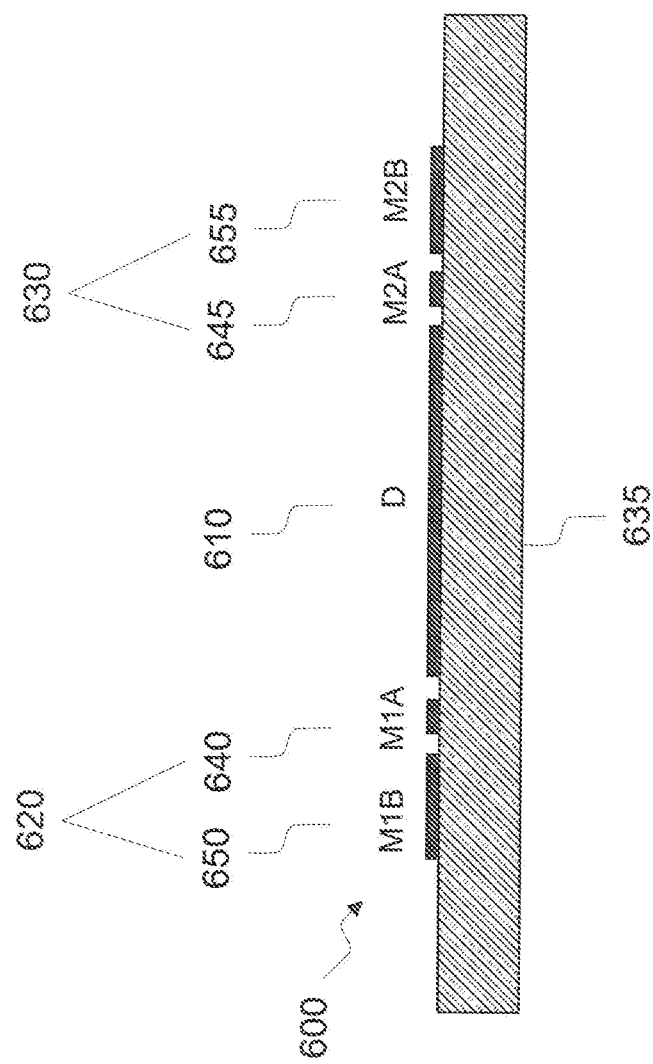
FIG. 6A is a drawing depicting an alternative arrangement of electrodes in accordance with another embodiment of the present invention.

FIG. 6A is a drawing depicting an alternative arrangement of electrodes in accordance with another embodiment of the present invention. Similarly to the previous embodiment, an electrode arrangement 600 for a microfluidic device may include a drive electrode (D) 610, a first set of measurement electrodes 620, and second set of measurement electrodes 630 formed on a substrate 635. In this example arrangement, the first measurement sub-electrodes of each set of measurement electrodes 640, 645 (M1A, M2A) may be chosen to have a different width than the second measurement sub-electrodes of each set of measurement electrodes 650, 655 (M1B, M2B) in the x-direction along the substrate. In the example arrangement of FIG. 6A, the first sub-electrodes 640, 645 may, for example, be less wide than the second sub-electrodes 650, 655. Adjustment of the sub-electrode lengths enables the relative magnitude of the impedance measurements associated with the first and second measurement sub-electrodes to be adjusted. Advantageously, this may allow the dynamic range and signal-to-noise ratio of the impedance measurement circuits to be optimized.

Figure 6B:
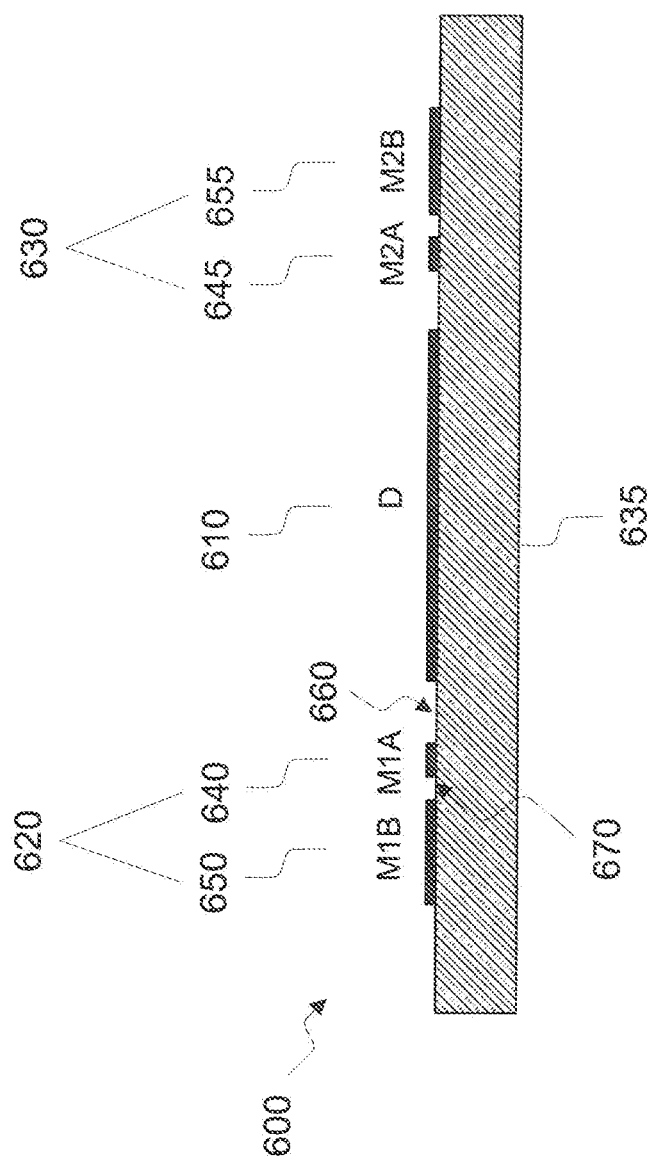
FIG. 6B is a drawing depicting an alternative arrangement of electrodes in accordance with another embodiment of the present invention.

Alternatively or additionally, the same effect and advantage may be achieved by choosing the spacing between the first sub-electrodes, second sub-electrodes and drive electrode to be different. FIG. 6B is a drawing depicting an alternative arrangement of electrodes in which a different spacing is provided as between different sub-electrodes. Generally, within each pair of measurement sub-electrodes, a first spacing 660 between the first measurement sub-electrode 640, 645 and the drive electrode 610 differs from a second spacing 670 between the first measurement sub-electrode 640, 645 and the respective second measurement sub-electrode 650, 655. In this particular example arrangement of FIG. 6B, the first spacing is wider than the second spacing. Other differences of spacing may be employed to optimize performance.

Figure 7:
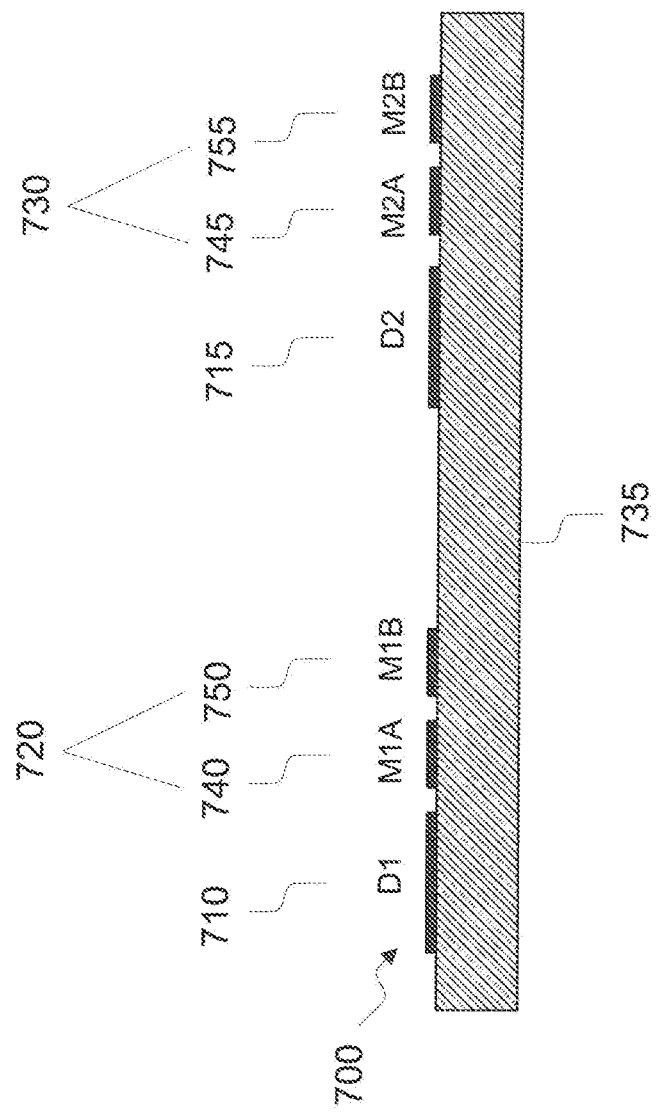
FIG. 7 is a drawing depicting a further alternative arrangement of electrodes in accordance with another embodiment of the present invention.

FIG. 7 is a drawing depicting a further alternative arrangement of electrodes in accordance with another embodiment of the present invention. In this example arrangement, an electrode arrangement 700 for a microfluidic device may include a first drive electrode (D1) 710 and a second drive electrode (D2) 715 that are formed on a substrate 735 alongside a first set of measurement electrodes 720 and a second set of measurement electrodes 730. The first measurement sub-electrodes of each set of measurement electrodes 740, 745 (M1A, M2A) are adjacent to the corresponding drive electrodes 710, 715, and the second measurement sub-electrodes of each set of measurement electrodes 750, 755 (M1B, M2B) are separated from the corresponding drive electrodes 710, 715 by the first sub-electrodes 740, 745. The first drive electrode 710 and first set of measurement electrodes 720 may be sufficiently separated from the second drive electrode 715 and second set of measurement electrodes 730 that they are not in electrical communication, i.e. there are no electric field lines that couple between the electrodes 710, 730 and the electrodes 715, 720. In operation the drive electrodes 710, 715 may be connected to the same voltage stimulus. An advantage of this arrangement is that it may provide improved matching between the first measured impedances, $Z_{1A}$ and $Z_{2A}$, and between the second measured impedances, $Z_{1B}$ and $Z_{2B}$. Accordingly, the arrangement of FIG. 7 may allow a more accurate discrimination between particles of different particular diameters, and hence a more accurate particle count, to be made.

In another aspect of the invention, a microfluidic impedance cytometry device in accordance with any of the above embodiments is integrated or incorporated within an electrowetting-on-dielectric (EWOD) device. As is well known in the art, EWOD devices may be used to manipulate droplets of fluid by electronic means using electrowetting techniques. Integration of a microfluidic impedance cytometry device within an EWOD device allows the number of particles within a droplet to be counted. With an impedance cytometry device of sufficient accuracy, for example as described in this disclosure, the number of particles of a particular size and/or diameter may additionally be counted.

Figure 8:
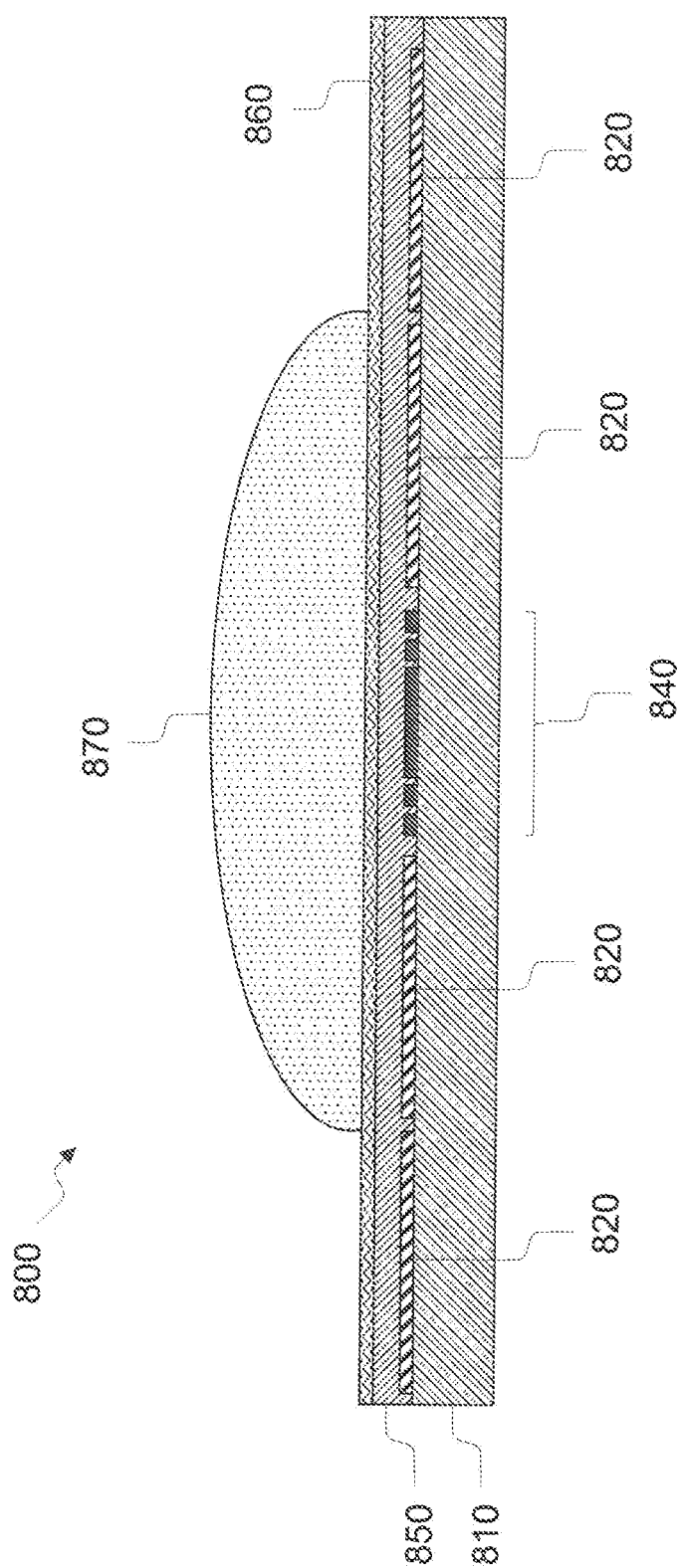
FIG. 8 is a drawing depicting a cross-section of an exemplary EWOD device in accordance with embodiments of the present invention.

In an exemplary embodiment of an EWOD device, electrodes for impedance cytometry are formed on the same substrate as the electrodes that are used to apply the electrowetting force for the actuation of droplets on the surface of the substrate. FIG. 8 is a drawing depicting a cross-section of an exemplary EWOD device 800. As illustrated in the cross-section diagram of the example device of FIG. 8, cytometry electrodes 840 and electrowetting electrodes 820 are formed on the same plane on the surface of a substrate 810. Alternatively, the cytometry electrodes and electrowetting electrodes may be formed in different layers on the same substrate. An insulating layer 850 and a hydrophobic coating layer 860 are formed on top of the cytometry electrodes and electrowetting electrodes, and the insulating layer separates the electrodes from the fluid droplet 870. The cytometry electrodes 840 and electrowetting electrodes 820 may be connected to circuits that control their respective functions. Such circuits may be external to the device or may be formed on the substrate by, for example, thin film transistors. In operation, the electrowetting electrodes 820 may cause the fluid droplet to pass over the cytometry electrodes 840. Accordingly, particles within the droplet will be caused to pass over the cytometry electrodes and may be measured and counted. The concentration of particles within the droplet may be controlled and the size and shape of the droplet may be controlled to ensure that generally only one particle passes over the cytometry electrodes 840 at any one time. An accurate count of particles and determination of particle size and/or diameter may therefore be made.

Figure 9:
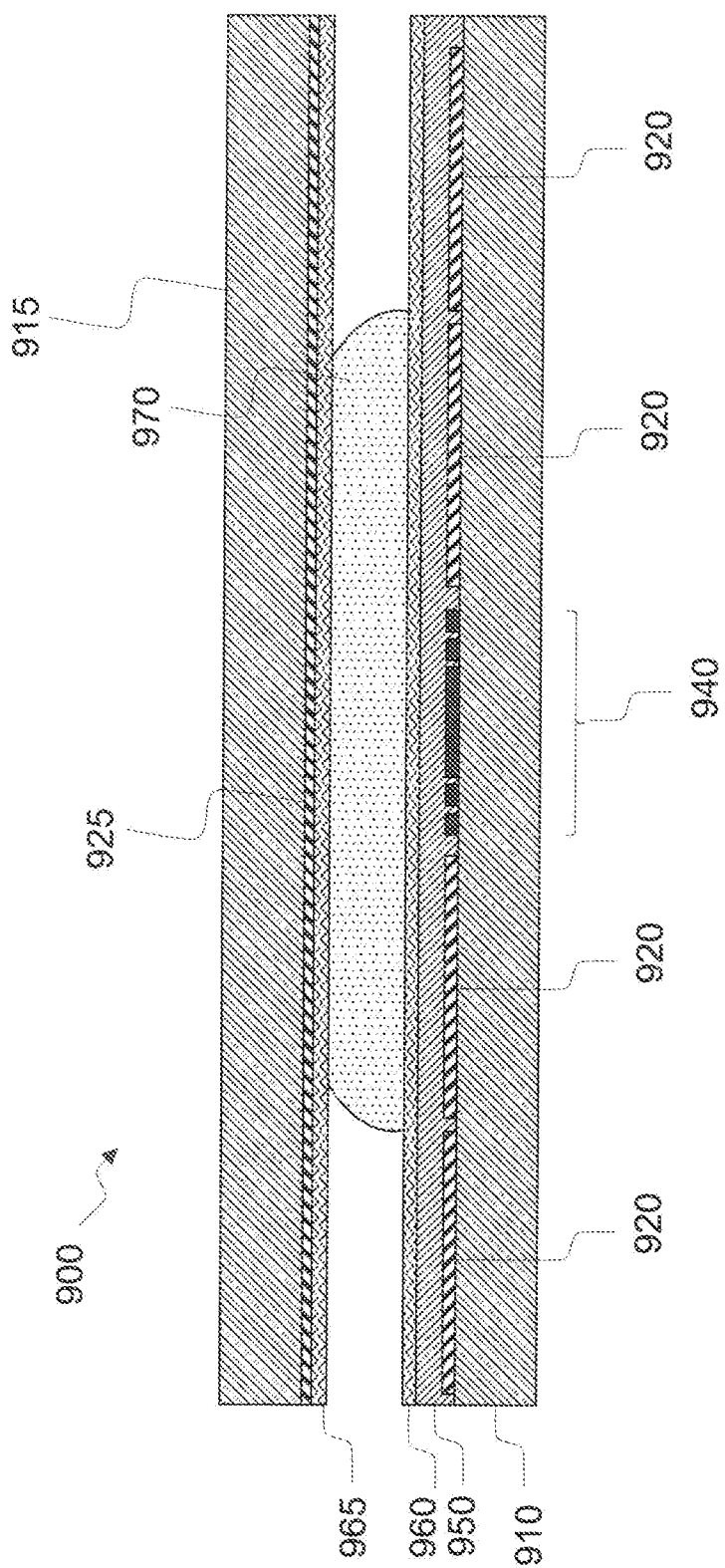
FIG. 9 is a drawing depicting an exemplary microfluidic impedance cytometry device integrated within an EWOD device comprising two substrates in accordance with embodiments of the present invention.

FIG. 9 is a drawing depicting in cross-section an exemplary microfluidic impedance cytometry device integrated within an EWOD device 900 comprising two substrates in accordance with embodiments of the present invention. In the example of FIG. 9, similarly to that of FIG. 8, the impedance cytometry electrodes are formed on a first substrate of the electrowetting device alongside the electrowetting electrodes. Cytometry electrodes 940 and electrowetting electrodes 920 are formed on the same plane on the surface of a first substrate 910. Alternatively, the cytometry electrodes and electrowetting electrodes may be formed in different layers on the same substrate. An insulating layer 950 and a first hydrophobic coating layer 960 are formed on top of the cytometry electrodes and electrowetting electrodes, and the insulating layer separates the electrodes from the fluid droplet 970. The cytometry electrodes 940 and electrowetting electrodes 920 may be connected to circuits that control their respective functions. In the two-substrate configuration, the EWOD device 900 further includes a second substrate 915 opposite from the substrate 910 relative to the microfluidic channel where the droplet 970 resides. A common reference electrode 925 is formed on the second substrate 915, and a second hydrophobic coating layer 965 is formed on the reference electrode 925. In operation, an electrowetting drive voltage is generated as a voltage difference between the electrowetting electrode 920 and the reference electrode 925

Figure 10:
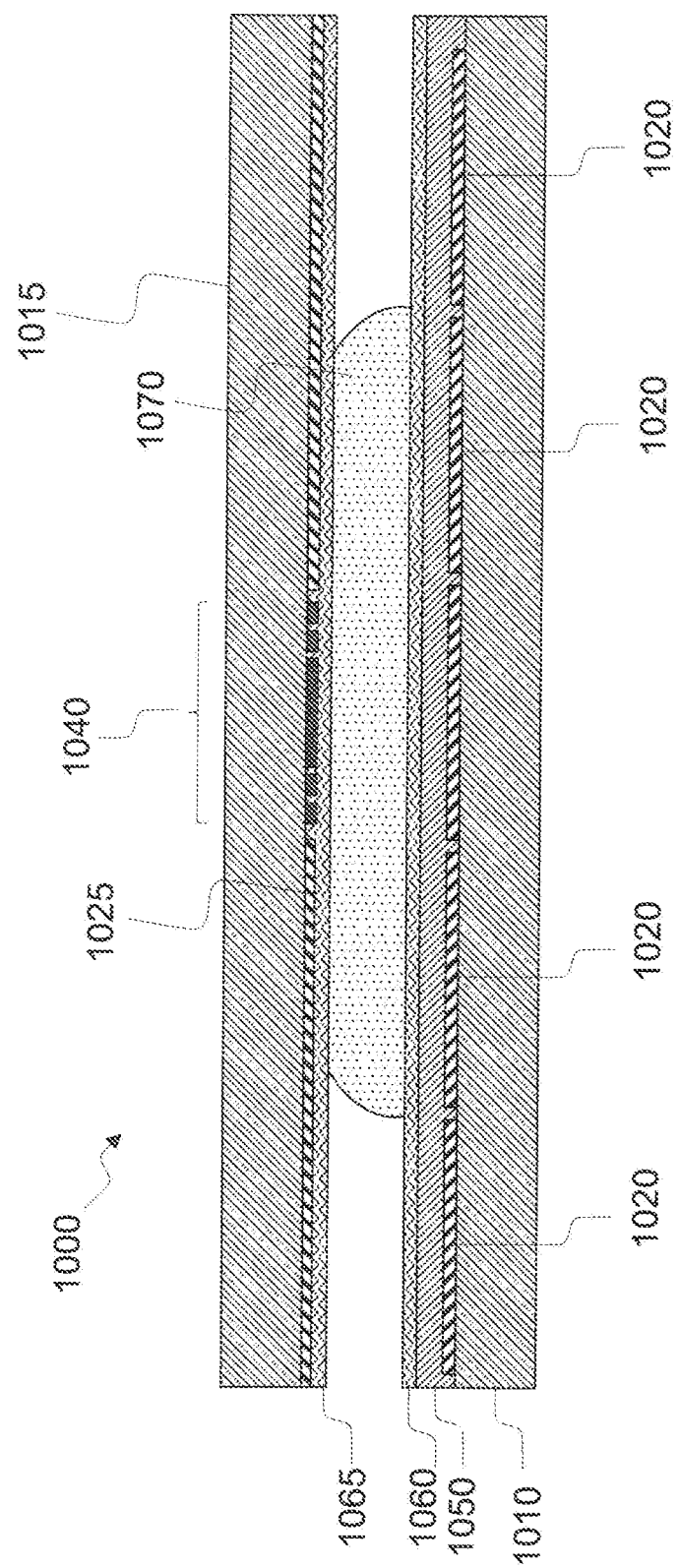
FIG. 10 is a drawing depicting another exemplary microfluidic impedance cytometry device integrated within an EWOD device comprising two substrates in accordance with embodiments of the present invention.

FIG. 10 is a drawing depicting in cross-section another exemplary microfluidic impedance cytometry device integrated within an EWOD device 1000 comprising two substrates in accordance with embodiments of the present invention. The configuration of FIG. 10 bears similarity to that of FIG. 9, with the difference that in the embodiment of FIG. 10, the cytometry electrodes of a microfluidic impedance cytometry device are formed alongside the common reference electrode on the second substrate of an EWOD device. An advantage of this embodiment is that droplet manipulation is not hindered by the presence of the cytometry electrodes. Electrowetting electrodes 1020 are formed on the surface of a first substrate 1010. An insulating layer 1050 and a first hydrophobic coating layer 1060 are formed on top of the electrowetting electrodes, and the insulating layer separates the electrodes from the fluid droplet 1070. In the two-substrate configuration, the EWOD device 1000 further includes a second substrate 1015 opposite from the substrate 1010 relative to the microfluidic channel where the droplet 1070 resides. Common reference electrodes 1025 are formed on the second substrate 1015, and a second hydrophobic coating layer 1065 is formed on the reference electrodes 1025. In operation, an electrowetting drive voltage is generated as a voltage difference between the electrowetting electrode 1020 and the reference electrode 1025. In the example of FIG. 10, cytometry electrodes 1040 and common reference electrodes 1025 are formed on the same plane on the surface of the second substrate 1015. Alternatively, the cytometry electrodes and common reference electrodes may be formed in different layers on the same substrate. As in the previous embodiment, the cytometry electrodes 1040 and electrowetting electrodes 1020 may be connected to circuits that control their respective functions.

In an exemplary mode of operation of an EWOD device including an impedance cytometry device, a control circuit may be connected to the cytometry electrodes that enables the electrode function to be switched dynamically between a cytometry function in which a particle size is determined as to a particle in a fluid droplet as described above, and an electrowetting function in which a droplet manipulation is performed on the fluid droplet. Droplet manipulations, for example, may include forming droplets, moving droplets along the electrowetting array, splitting droplets, mixing droplets, determining or sensing droplet properties, and other droplet manipulations as may be known in the art of EWOD devices. The control circuit may be external to the device or may be formed on the substrate by, for example, thin film transistors.

Figure 11:
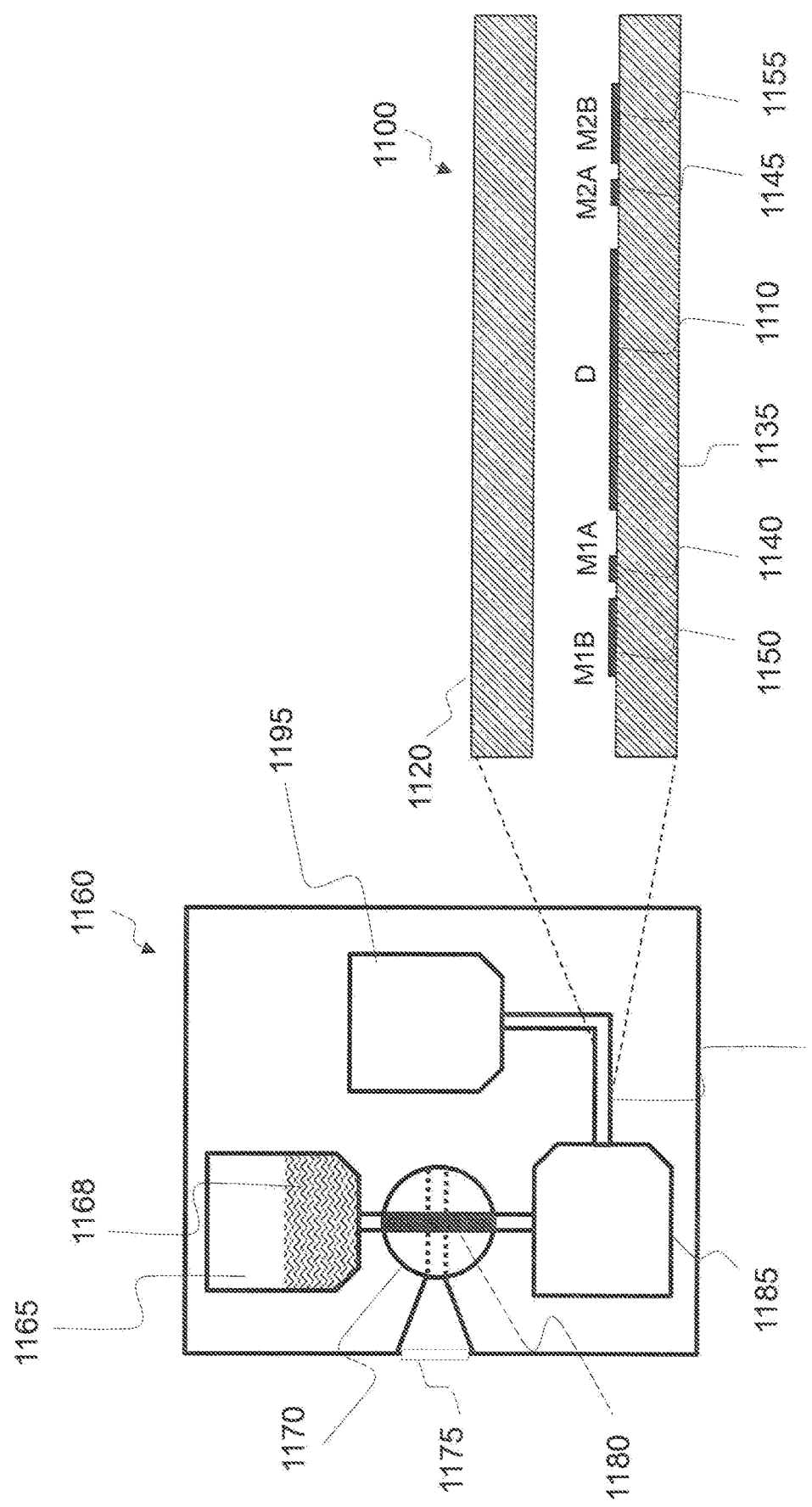
FIG. 11 is drawing depicting a configuration of incorporating an impedance cytometer device into a microfluidic device for counting blood cells in accordance with embodiments of the present invention.

FIG. 11 teaches one method of incorporating an impedance cytometer 1100 into a microfluidic device 1160 for counting blood cells. The microfluidic device 1160 includes a first chamber 1165 partially filled with a solution 1168, a mixing chamber 1185, a fluidic channel 1190 with an integrated impedance cytometer 1100 in fluid communication with a rotating valve 1170, and a waste chamber 1195. A whole blood sample is input through aperture 1175 and into the rotating valve 1170 with an internal channel that can meter a predetermined small volume of blood 1180. Generally, cells are counted based on impedance measurements taken at the impedance cytometry device Components common to previous embodiments are denoted by reference numerals index by 1100.

Typically, 1 µl of whole human blood contains ~5 million red blood cells (RBCs), ~10,000 white blood cells (WBCs), and ~500,000 platelets. To accurately count the number of WBCs, the RBCs must be removed, i.e., lysed within the mixing chamber 1185. To enable the RBCs to be counted accurately, a whole blood sample is diluted, for example in a 1:5,000 to 1:40,000 ratio. The whole blood sample may be diluted in a 1:10,000 to 1:20,000 ratio, or diluted in a 1:10,000 ratio. Platelets are counted preferably alongside the RBCs. It follows that there are two different sample preparation protocols—one for WBCs, and the other for RBCs and platelets combined.

In one embodiment, the solution 1168 may be a lysis solution to lyse RBCs so that the WBCs can be differentiated and counted (up to a 5-part differential). The lysis solution is mixed with the sample input within the mixing chamber 1185, and the product of the mixing is then communicated through the fluidic channel 1190 with the integrated impedance cytometer 1100 for cell counting. The lysis reagent is any reagent mixture containing a chemical known to lyse RBCs, such as for example saponins, quaternary ammonium salts, or the like. Preferably, the lysis reagent used contains saponin. The lysis reagent may be 0.12% v/v formic acid and 0.05% w/v saponin.

Optionally and/or additionally, a quench reagent may be further added after a pre-determined length of time for optimal lysis, wherein the quench reagent is any mixture known to halt or substantially reduce the rate of RBC lysis. The quench reagent may be 0.6% w/v sodium carbonate and 3% w/v sodium chloride. In exemplary embodiments, the blood:lysis:quench reagents are mixed in a ratio of 1:12:5.3. (See embodiments in U.S. Pat. No. 9,440,233 B2 Dothie et al, or U.S. Pat. No. 9,283,560 B2 Dothie).

Alternatively, the solution 1168 could be a diluent solution so that RBCs and platelets can be sufficiently diluted to enable accurate quantification of RBCs and platelets. The diluent reagent is one compatible with RBCs and platelets. Compatible implies that the reagent in question does not cause serious degradation to the sample, nor promotes clotting of either the RBCs or the platelets. Dilutent reagents may include, but are not limited to, PBS, running buffer (comprising PBS, 2 mM EDTA, 0.5% BSA), and the like.

The embodiment may further include performing a haemoglobin measurement in a haemoglobin measurement chamber, such is in the chamber 1165 holding the solution 1168. For haemoglobin to be measured accurately, the RBCs must be lysed. It follows that the most preferable position for the haemoglobin measurement is after the RBCs have been lysed in the WBC counting prototcol. It is further preferable to convert the haemoglobin into a stable oxidized form (methemoglobin) by adding chemical haemoglobin reagent mixtures. Suitable reagents include, but are not limited to, Drabkins's reagent (which contains sodium bicarbonate, potassium ferricyanide and potassium cyanide and converts haemoglobin into cyanmethemoglobin), ferrocyanide, or the like. Such haemoglobin reagents could be pre-dried in the haemoglobin measurement chamber. In practice, haemoglobin is converted to cyanmethemoglobin (e.g. by reacting the blood with a Drabkin's reagent) and measured spectrophotometrically (the reacted Drabkin's reagent and haemoglobin form a stable, coloured end-product). A simple LED/photodiode combination can be employed for the quantitative, colourimetric determination of blood haemoglobin using absorbance in accordance with Beer's law, as is known in the art.

After cell counting, and the haemoglobin measurement, the processed blood samples are collected in a waste chamber.

The two different sample processing protocols for WBCs and RBCs/platelets may be carried out on separate cartridges, and the cells of interest counted on separate impedance sensors. An alternative embodiment would carry out the processing protocols for WBCs and RBCs/platelets in parallel, and then count e.g. the WBCs then the RBCs/platelets on a single impedance chip in series. In a further alternative embodiment, the two different sample processing protocols could be carried out in series and the e.g. WBCs followed by the RBCs/platelets counted on a single impedance sensor.

Alternatively and/or additionally, co-planar impedance cytometers as described in this patent can be integrated into microfluidic blood cell counters of the types described in the following patents; U.S. Pat. No. 7,771,658 B2 Larsen et al, U.S. Pat. No. 9,440,233 B2 Dothie et al, or U.S. Pat. No. 9,283,560 B2 Dothie.

Figure 12A:
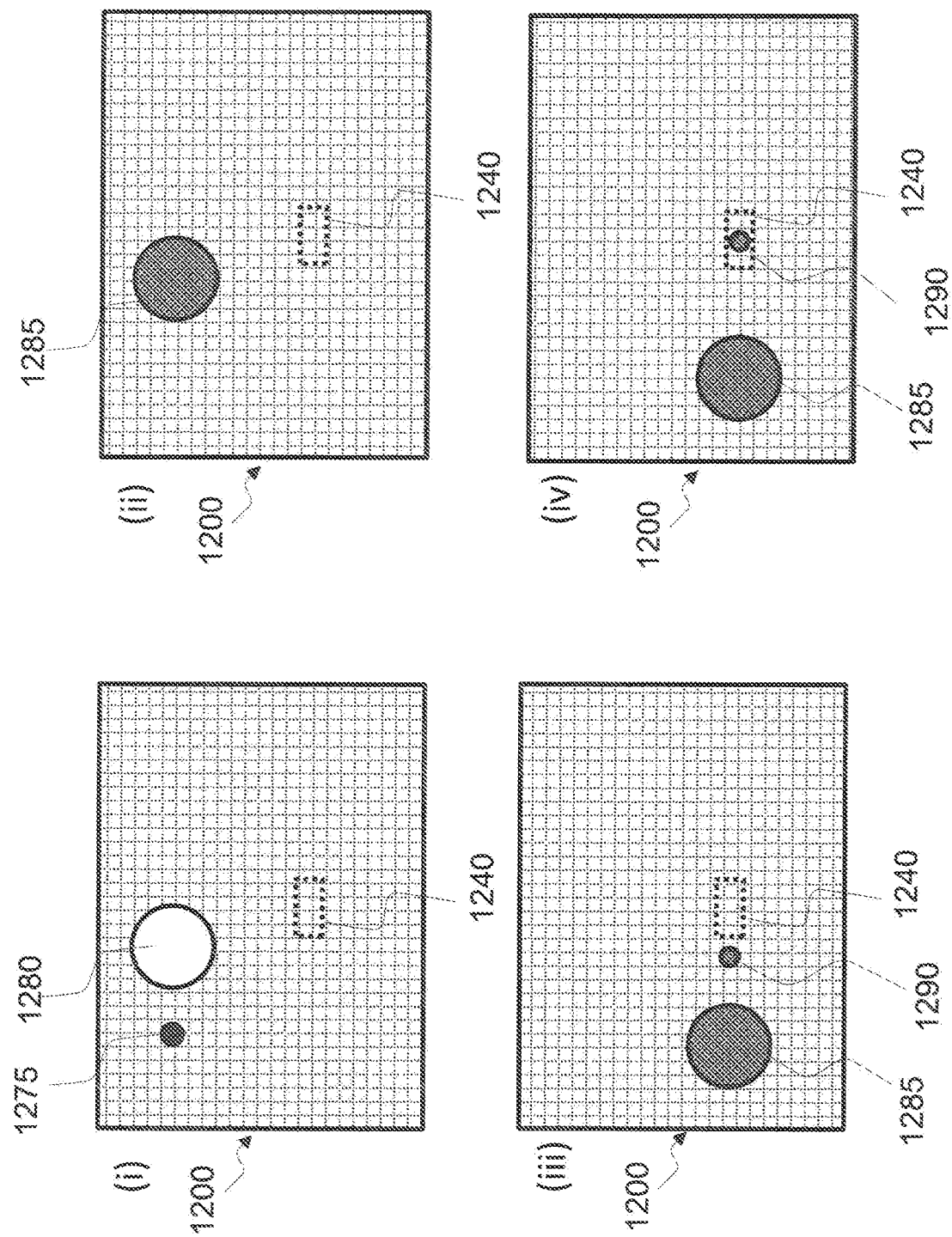

FIG. 12A teaches an EWOD device 1200 with an integrated impedance cytometer 1240. A droplet of whole blood 1275 is merged with a solution droplet 1280 using electrowetting to produce a mixed droplet 1285. A daughter droplet 1290 is split from the mixed droplet 1285 using electrowetting and moved, via electrowetting forces, through the integrated impedance cytometer 1240. The solution droplet 1280 can be either a lysis solution to lyse RBCs so that the WBCs can be differentiated and counted, or it can be a diluent solution so that RBCs and platelets can be sufficiently diluted to enable accurate quantification of RBCs and platelets.

EWOD technology is well suited to merging, mixing, splitting and moving droplets, offering several ease-of-workflow benefits compared to mechanical microfluidic cartridges.

FIG. 12B describes an EWOD device 1200 for counting blood cells where the impedance cytometer 1240 is integrated into the top plate 1215 of the EWOD device 1200. FIG. 12C teaches an EWOD device 1200 for counting blood cells where the impedance cytometer 1240 is integrated into the bottom plate 1210 of the EWOD device 1200. Components common to previous embodiments are denoted by reference numerals index by 1200.

The two different sample processing protocols for WBCs and RBCs/platelets may be carried out simultaneously and the cells of interest counted on separate impedance sensors. An alternative embodiment would carry out the processing protocols for WBCs and RBCs/platelets in parallel, and then count e.g. the WBCs then the RBCs/platelets on a single impedance chip in series. In a further alternative embodiment, the two different sample processing protocols could be carried out in series and the e.g. WBCs followed by the RBCs/platelets counted on a single impedance sensor.

An aspect of the invention, therefore, is an impedance cytometry device including a substrate and an electrode arrangement deposited on the substrate in a co-planar fashion, the electrode arrangement comprising a drive electrode and a plurality of measurement electrodes located in a same plane as the drive electrode. The plurality of measurement electrodes includes at least two pairs of measurement sub-electrodes, each pair of measurement sub-electrodes including a first measurement sub-electrode positioned adjacent to the drive electrode, and a second measurement sub-electrode separated from the drive electrode by a respective first measurement electrode. The impedance cytometry device may include one or more of the following features, either individually or in combination.

In an exemplary embodiment of the impedance cytometry device, the device further includes an impedance measurement unit configured to measure impedance differences between measurement sub-electrodes of the plurality of measurement electrodes.

In an exemplary embodiment of the impedance cytometry device, the impedance measurement unit comprises: a voltage stimulus unit configured to supply a stimulus voltage to the drive electrode; a sensing unit configured to measure current signals generated by the measurement sub-electrodes in response to the stimulus voltage; and a control unit configured to receive output signals from the sensing unit and calculate the impedance differences, wherein the control unit processes the impedance differences to provide a measurement of particles passing the measurement electrodes.

In an exemplary embodiment of the impedance cytometry device, the sensing unit comprises a differential sensing circuit configured to measure differential current signals between first measurement sub-electrodes in different pairs of measurement electrodes, and to measure differential current signals between second measurement sub-electrodes in different pairs of measurement electrodes.

In an exemplary embodiment of the impedance cytometry device, a width of the first measurement sub-electrodes along the substrate differs from a width of the second measurement sub-electrodes along the substrate.

In an exemplary embodiment of the impedance cytometry device, within each pair of measurement sub-electrodes, a spacing between the first measurement sub-electrode and the drive electrode differs from a spacing between the first measurement sub-electrode and the second measurement sub-electrode.

In an exemplary embodiment of the impedance cytometry device, different pairs of measurement sub-electrodes are located on opposite sides of a single drive electrode.

In an exemplary embodiment of the impedance cytometry device, the electrode arrangement comprises a first drive electrode and a second drive electrode; a first pair of measurement sub-electrodes includes a first measurement sub-electrode positioned adjacent to the first drive electrode, and a second measurement sub-electrode separated from the first drive electrode by the first measurement electrode; and a second pair of measurement electrodes includes another first measurement sub-electrode positioned adjacent to the second drive electrode, and another second measurement sub-electrode separated from the second drive electrode by the another first measurement electrode.

In an exemplary embodiment of the impedance cytometry device, a width and/or separation of the first and second measurement sub-electrodes is between 1-50 µm.

Another aspect of the invention is an electrowetting on dielectric (EWOD) device including a substrate assembly that defines a microfluidic channel and includes electrowetting electrodes; and an impedance cytometry device in accordance with any of the embodiments. The EWOD device may include one or more of the following features, either individually or in combination.

In an exemplary embodiment of the EWOD device, the substrate assembly comprises a substrate onto which is deposited the electrode arrangement of the impedance cytometry device and the electrowetting electrodes, an insulator layer deposited on the substrate, and a hydrophobic coating deposited on insulator layer to define the microfluidic channel.

In an exemplary embodiment of the EWOD device, the electrode arrangement of the impedance cytometry device and the electrowetting electrodes are formed on a same plane on a surface of the substrate.

In an exemplary embodiment of the EWOD device, the device includes a first substrate assembly and a second substrate assembly; wherein one of the first or second substrate assemblies includes electrowetting electrodes and the other of the first or second substrate assembly includes a common reference electrode, and the first substrate assembly and the second substrate assembly are spaced apart to define a microfluidic channel between the first and second substrate assemblies; and an impedance cytometry device of any of claims 1-9 incorporated into one of the first substrate assembly or the second substrate assembly.

In an exemplary embodiment of the EWOD device, the first substrate assembly comprises a first substrate onto which is deposited the electrode arrangement of the impedance cytometry device and the electrowetting electrodes, an insulator layer deposited on the first substrate, and a hydrophobic coating deposited on insulator layer to define the microfluidic channel; and the second substrate assembly comprises a second substrate onto which is deposited the common reference electrode, and a second hydrophobic coating deposited on common reference electrode to define the microfluidic channel.

In an exemplary embodiment of the EWOD device, the first substrate assembly comprises a first substrate onto which is deposited the electrowetting electrodes, an insulator layer deposited on the first substrate, and a hydrophobic coating deposited on insulator layer to define the microfluidic channel; and the second substrate assembly comprises a second substrate onto which is deposited the electrode arrangement of the impedance cytometry device and the common reference electrode, and a second hydrophobic coating deposited on common reference electrode to define the microfluidic channel.

Another aspect of the invention is a microfluidic cell counting device having the enhanced impedance cytometry device. In exemplary embodiments, the microfluidic cell counting device includes a chamber for receiving a reagent solution; a rotating valve for receiving a sample input, the rotating valve including an internal channel that meters a predetermined amount of the sample input; a mixing chamber in fluid communication with the rotating valve, wherein the sample input and reagent solution are communicated to the mixing chamber by operation of the rotating valve and mixed within the mixing chamber; and a fluidic channel in fluid communication with the mixing chamber, the fluidic channel including the impedance cytometry device of any of the embodiments incorporated into the fluidic channel, wherein cells in the sample input are counted based on impedance measurements taken at the impedance cytometry device.

Another aspect of the invention is a method of measuring particle size in a fluid sample using the enhanced impedance cytometry device. In exemplary embodiments, the measuring method includes the steps of: passing the fluid sample containing particles through an impedance cytometry device that defines a microfluidic channel, supplying a voltage stimulus to the drive electrode; measuring current signals generated on the measurement sub-electrodes to determine impedance changes generated in response to a particle passing through electric fields generated by the measurement electrodes; and determining a particle size based on the impedance changes. The measuring method may include one or more of the following features, either individually or in combination.

In an exemplary embodiment of the measuring method, measuring current signals generated on the measurement sub-electrodes comprises measuring differential current signals between pairs of measurement sub-electrodes.

In an exemplary embodiment of the measuring method, measuring differential current signals comprises measuring differential current signals between the first measurement sub-electrodes in first and second pairs of measurement electrodes, and between the second measurement sub-electrodes in the first and second pairs of measurement electrodes.

In an exemplary embodiment of the measuring method, determining the impedance changes comprises: determining impedance differentials within first regions of the microfluidic channel in which electric fields are formed between the first measurement sub-electrodes and the drive electrode; and determining impedance differentials within second regions of the microfluidic channel in which electric fields are formed between the second measurement sub-electrodes and the drive electrode; wherein the first regions are closer to the electrode arrangement than the second regions.

In an exemplary embodiment of the measuring method, the method further includes determining a ratio between peak magnitudes of the differential impedances in the first regions and the second regions; calculating a processed impedance value as a function of output voltages based on the measured differential impedances, including using the ratio of the peak magnitudes of the differential impedances; and determining particle size based on the processed impedance value.

In an exemplary embodiment of the measuring method, the method further includes sizing the microfluidic channel and controlling a concentration of particles in the fluid such that only one particle passes through the impedance cytometry device at a time.

In an exemplary embodiment of the measuring method, the method further includes incorporating the impedance cytometry device into an electrowetting on dielectric (EWOD) device, wherein the impedance cytometry device is incorporated into one of the first substrate assembly or the second substrate assembly.

In an exemplary embodiment of the measuring method, the method further includes switching dynamically between a cytometry function in which a particle size is determined as to a particle in a fluid droplet, and an electrowetting function in which a droplet manipulation is performed on the fluid droplet.

In an exemplary embodiment of the measuring method, the method further includes incorporating the impedance cytometry device into a microfluidic cell counting device; inputting the reagent solution into the chamber; inputting the sample input into the rotating valve, thereby metering the sample input; operating the rotating valve to communicate the sample input and a portion of the reagent solution into the mixing chamber; wherein the sample input and the portion of the reagent solution are mixed within the mixing chamber; and communicating the mixed sample input and reagent solution through the fluidic channel to the impedance cytometry device, wherein cells in the sample input are counted based on impedance measurements taken at the impedance cytometry.

In an exemplary embodiment of the measuring method, the sample input is a blood sample, and the method further comprises counting one or more red blood cells, white blood cells, and platelets in the sample input.

Although the invention has been shown and described with respect to a certain embodiment or embodiments, equivalent alterations and modifications may occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein exemplary embodiment or embodiments of the invention. In addition, while a particular feature of the invention may have been described above with respect to only one or more of several embodiments, such feature may be combined with one or more other features of the other embodiments, as may be desired and advantageous for any given or particular application.

INDUSTRIAL APPLICABILITY

The present invention finds application as a method of counting particles within a microfluidic device. The present invention additionally finds application as a method of counting particles of a particular size, or diameter, within a microfluidic device. Such devices may be used, for example, to count cells such as bacterial, animal, plant or human cells within a sample of a biological fluid. Applications may include, for example, counting blood cells in human blood samples and providing a full blood cell count.

REFERENCE SIGNS LIST

100—microfluidic device
120—second substrate
130—first substrate
140—electrodes
150—microfluidic channel or gap
160—particles
170—fluid
180—spacer
210—drive electrode
220—first set of measurement electrodes
230—second set of measurement electrodes
240, 245—first measurement sub-electrode
250, 255—second measurement sub-electrode
260—first region
265—second region
270—impedance measurement unit
272—control unit
274—voltage stimulus unit
276—differential sensing unit
278—sensing unit
600—electrode arrangement
610—drive electrode
620—first set of measurement electrodes
630—second set of measurement electrodes
635—substrate
640, 645—first measurement sub-electrodes
650, 655—second measurement sub-electrodes
660—first spacing 670—second spacing
700—electrode arrangement
710—first drive electrode
715—second drive electrode
720—first set of measurement electrodes
730—second set of measurement electrodes
735—substrate
740, 745—first measurement sub-electrodes
750, 755—second measurement sub-electrodes
800—EWOD device
810—substrate
820—electrowetting electrodes
840—cytometry electrodes
850—insulating layer
860—hydrophobic coating layer
870—fluid droplet
900—EWOD device
910—first substrate
915—second substrate
920—electrowetting electrodes
925—reference electrode
940—cytometry electrodes
950—insulating layer
960—first hydrophobic coating layer
965—second hydrophobic coating layer
970—fluid droplet
1000—EWOD device
1010—first substrate
1015—second substrate
1020—electrowetting electrodes
1025—reference electrodes
1040—cytometry electrodes
1050—insulating layer
1060—first hydrophobic coating layer
1065—second hydrophobic coating layer
1070—fluid droplet
1100—impedance cytometer
1160—microfluidic device
1165—first chamber
1168—solution
1170—rotating valve
1175—aperture
1180—small volume of blood
1185—mixing chamber
1190—fluidic channel
1195—waste chamber
1200—EWOD device
1210—bottom plate
1215—top plate
1240—impedance cytometer
1275—droplet of whole blood
1280—solution droplet
1285—mixed droplet
1290—daughter droplet

What is claimed is:

1. An impedance cytometry device comprising:
a substrate; and
an electrode arrangement deposited on the substrate in a co-planar fashion, the electrode arrangement comprising a drive electrode and a plurality of measurement electrodes located in a same plane as the drive electrode;
wherein the plurality of measurement electrodes includes at least two pairs of measurement sub-electrodes, each pair of measurement sub-electrodes including a first measurement sub-electrode positioned adjacent to the drive electrode, and a second measurement sub-electrode separated from the drive electrode by a respective first measurement electrode;
a sensing unit configured to measure current signals generated by the measurement sub-electrodes in response to the stimulus voltage, wherein the first measurement sub-electrodes are electrically connected to the sensing unit to generate a differential signal between the first measurement sub-electrodes of the at least two pairs of measurement sub-electrodes, and wherein the second measurement sub-electrodes are electronically connected to the sensing unit to generate a differential signal between the second measurement sub-electrodes of the at least two pairs of measurement sub-electrodes; and
a control unit configured to receive the differential signals from the sensing unit and calculate impedance differences between the first measurement sub-electrodes of the at least two pairs of measurement sub-electrodes and between the second measurement sub-electrodes of the at least two pairs of measurement sub-electrodes, wherein the control unit processes the impedance differences to provide at least one of a count measurement and a diameter measurement of particles passing the measurement electrodes.

2. The impedance cytometry device of claim 1, wherein the sensing unit comprises a differential sensing circuit configured to measure differential current signals between first measurement sub-electrodes in different pairs of measurement electrodes, and to measure differential current signals between second measurement sub-electrodes in different pairs of measurement electrodes.

3. The impedance cytometry device of claim 1, wherein a width of the first measurement sub-electrodes along the substrate differs from a width of the second measurement sub-electrodes along the substrate.

4. The impedance cytometry device of claim 1, wherein within each pair of measurement sub-electrodes, a spacing between the first measurement sub-electrode and the drive electrode differs from a spacing between the first measurement sub-electrode and the second measurement sub-electrode.

5. The impedance cytometry device of claim 1, wherein different pairs of measurement sub-electrodes are located on opposite sides of a single drive electrode.

6. The impedance cytometry device of claim 1, wherein:
the electrode arrangement comprises a first drive electrode and a second drive electrode;
a first pair of measurement sub-electrodes includes a first measurement sub-electrode positioned adjacent to the first drive electrode, and a second measurement sub-electrode separated from the first drive electrode by the first measurement electrode; and
a second pair of measurement electrodes includes another first measurement sub-electrode positioned adjacent to the second drive electrode, and another second measurement sub-electrode separated from the second drive electrode by the another first measurement electrode.

7. The impedance cytometry device of claim 1, wherein a width and/or separation of the first and second measurement sub-electrodes is between 1-50 µm.

8. An electrowetting on dielectric (EWOD) device comprising:
a substrate assembly that defines a microfluidic channel and includes electrowetting electrodes; and
an impedance cytometry device of claim 1 incorporated into the substrate assembly.

9. The EWOD device of claim 8, wherein the substrate assembly comprises a substrate onto which is deposited the electrode arrangement of the impedance cytometry device and the electrowetting electrodes, an insulator layer deposited on the substrate, and a hydrophobic coating deposited on insulator layer to define the microfluidic channel.

10. The EWOD device of claim 9, wherein the electrode arrangement of the impedance cytometry device and the electrowetting electrodes are formed on a same plane on a surface of the substrate.

11. The EWOD device of claim 8, wherein the control circuit further is configured to dynamically switch operation of the drive electrode and the measurement electrodes between a cytometry function for performing the count and diameter measurement of particles passing the measurement electrodes, and an electrowetting function for performing electrowetting droplet manipulations.

12. An electrowetting on dielectric (EWOD) device comprising:
a first substrate assembly and a second substrate assembly;
wherein one of the first or second substrate assemblies includes electrowetting electrodes and the other of the first or second substrate assembly includes a common reference electrode, and the first substrate assembly and the second substrate assembly are spaced apart to define a microfluidic channel between the first and second substrate assemblies; and
an impedance cytometry device of claim 1 incorporated into one of the first substrate assembly or the second substrate assembly.

13. The EWOD device of claim 12, wherein:
the first substrate assembly comprises a first substrate onto which is deposited the electrode arrangement of the impedance cytometry device and the electrowetting electrodes, an insulator layer deposited on the first substrate, and a hydrophobic coating deposited on insulator layer to define the microfluidic channel; and
the second substrate assembly comprises a second substrate onto which is deposited the common reference electrode, and a second hydrophobic coating deposited on common reference electrode to define the microfluidic channel.

14. The EWOD device of claim 12, wherein:
the first substrate assembly comprises a first substrate onto which is deposited the electrowetting electrodes, an insulator layer deposited on the first substrate, and a hydrophobic coating deposited on insulator layer to define the microfluidic channel; and
the second substrate assembly comprises a second substrate onto which is deposited the electrode arrangement of the impedance cytometry device and the common reference electrode, and a second hydrophobic coating deposited on common reference electrode to define the microfluidic channel.

* * * * *